US011696957B2

(12) United States Patent
Yu

(10) Patent No.: US 11,696,957 B2
(45) Date of Patent: Jul. 11, 2023

(54) SINGLE PROTEIN-ENCAPSULATED PHARMACEUTICS FOR ENHANCING THERAPEUTIC EFFECTS

(71) Applicant: Sunstate Biosciences, LLC, Pasadena, CA (US)

(72) Inventor: Changjun Yu, Pasadena, CA (US)

(73) Assignee: Sunstate Biosciences, LLC, Pasadena, CA (US)

( * ) Notice: Subject to any disclaimer, the term of this patent is extended or adjusted under 35 U.S.C. 154(b) by 785 days.

(21) Appl. No.: 16/601,333

(22) Filed: Oct. 14, 2019

(65) Prior Publication Data

US 2020/0121804 A1    Apr. 23, 2020

Related U.S. Application Data

(60) Provisional application No. 62/746,964, filed on Oct. 17, 2018.

(51) Int. Cl.
| | |
|---|---|
| *A61K 31/136* | (2006.01) |
| *A61K 47/68* | (2017.01) |
| *A61K 47/64* | (2017.01) |
| *A61P 35/00* | (2006.01) |
| *A61K 31/337* | (2006.01) |
| *A61K 31/437* | (2006.01) |
| *A61K 31/4375* | (2006.01) |
| *A61K 31/496* | (2006.01) |
| *A61K 31/498* | (2006.01) |
| *A61K 31/519* | (2006.01) |
| *A61K 31/704* | (2006.01) |

(52) U.S. Cl.
CPC ........ *A61K 47/6803* (2017.08); *A61K 31/136* (2013.01); *A61K 31/337* (2013.01); *A61K 31/437* (2013.01); *A61K 31/4375* (2013.01); *A61K 31/496* (2013.01); *A61K 31/498* (2013.01); *A61K 31/519* (2013.01); *A61K 31/704* (2013.01); *A61K 47/643* (2017.08); *A61K 47/6809* (2017.08); *A61K 47/6835* (2017.08); *A61P 35/00* (2018.01)

(58) Field of Classification Search
None
See application file for complete search history.

(56) References Cited

PUBLICATIONS

Agudelo et al. (PLOS ONE 7(8):e43814 (13 Pages), 2012) (Year: 2012).*
Kilic et al (J Biomedical Nanotechnology 8(3):7 pages, 2011) (Year: 2011).*
Abbasi, S, et al., "Cationic Albumin Nanoparticles for Enhanced Drug Delivery to Treat Breast Cancer: Preparation and In Vitro Assessment", J Drug Deliv 686108, 9 pages (2012).

Agudelo, D, et al., "Probing the Binding Sites of Antibiotic Drugs Doxorubicin and N-(trifluoroacetyl) Doxorubicin with Human and Bovine Serum Albumins", Agudelo et al., PLOs One 7(8), e43814, 13 pages (2012).
Anderson, C, et al., "Perspective—FcRn transports albumin: relevance to immunology and medicine", Trends Immunol 27, 343-348 (2006).
Benjamin, R, et al., "Plasma Pharmacokinetics of Adriamycin and Its Metabolites in Humans with Normal Hepatic and Renal Function", Cancer Res 37, 1416-1420 (1977).
Carvalho, C, et al., "Doxorubicin: The Good, the Bad and the Ugly Effect", Curr Med Chem 16, 3267-3285 (2009).
Chatterjee, K, et al., "Doxorubicin cardiomyopathy", Cardilogy 115, 155-162 (2010).
Chaudhury, C, et al., "Albumin Binding to FcRn: Distinct from the FcRn-IgG Interaction", Biochemistry 45, 4983-4990 (2006).
Chaudhury, C, et al., "The Major Histocompatibility Complex-related Fc Receptor for IgG (FcRn) Binds Albumin and Prolongs Its Lifespan", J Exp Med 197, 315-322 (2003).
Commisso, C, et al., "Macropinocytosis of protein is an amino acid supply route in Ras-transformed cells", Nature 497, 633-637 (2013).
Eksborg, S, et al., "Pharmacokinetic study of IV infusions of adriamycin", Eur J Clin Pharmacol 28, 205-212 (1985).
Elzoghby, A, et al., "Albumin-based nanoparticles as potential controlled release drug delivery systems", J Control Release 15, 168-182 (2012).
Greene, R, et al., "Plasma pharmacokinetics of adriamycin and adriamycinol: implications for the design of in vitro experiments and treatment protocols", Cancer Res 43, 3417-3421 (1983).
Hoogenboezem, E, et al., "Harnessing albumin as a carrier for cancer therapies", Adv Drug Deliv Rev 130, 73-89 (2018).
Jin, G, et al., "Docetaxel-loaded PEG-albumin nanoparticles with improved antitumor efficiency against non-small cell lung cancer", Oncol Rep 36, 871-876 (2012).
Kamphorst, J, et al., "Human Pancreatic Cancer Tumors Are Nutrient Poor and Tumor Cells Actively Scavenge Extracellular Protein", Cancer Res 75, 544-553 (2015).
Kim, J, et al., "Albumin turnover: FcRn-mediated recycling saves as much albumin from degradation as the liver produces". Am J Physiol Gastrointest Liver Physiol 290, G352-360 (2006).
Kratz, F, et al., "Albumin as a drug carrier: Design of prodrugs, drug conjugates and nanoparticles", Journal of Controlled Release 132, 171-183 (2008).
Lomis, N, et al., "Human Serum Albumin Nanoparticles for Use in Cancer Drug Delivery: Process Optimization and In Vitro Characterization", Nanomaterials 6(6), 1-17 (2016).
Nateghian, N, et al., "Biotin/Folate-decorated Human Serum Albumin Nanoparticles of Docetaxel: Comparison of Chemically Conjugated Nanostructures and Physically Loaded Nanoparticles for Targeting of Breast Cancer", Chem Biol Drug Des 87, 69-82 (2016).
Patent Cooperation Treaty, International Searching Authority, Search Report and Written Opinion for PCT/US2019/056133, 16 pages, Feb. 5, 2020.

(Continued)

*Primary Examiner* — Craig D Ricci
(74) *Attorney, Agent, or Firm* — Viksnins Harris Padys Malen LLP

(57) ABSTRACT

The invention provides compositions comprising a single protein having one or more molecules of a pharmaceutical agent tightly bound therein. The compositions are useful to decrease the toxicity and/or to widen the therapeutic window of the pharmaceutical agent. The invention also provides methods for preparing such a composition.

3 Claims, 22 Drawing Sheets

(56) References Cited

PUBLICATIONS

Petersen, G, et al., "Meta-analysis of clinical and preclinical studies comparing the anticancer efficacy of liposomal versus conventional non-liposomal doxorubicin", J Control Release 232, 255-264 (2016).

Sebak, S, et al., "Human serum albumin nanoparticles as an efficient noscapine drug delivery system for potential use in breast cancer: preparation and in vitro analysis", Int J Nanomedicine 5, 525-532 (2010).

Shafei, A, et al., "A review on the efficacy and toxicity of different doxorubicin nanoparticles for targeted therapy in metastatic breast cancer", Biomed Pharmacolther 95, 1209-1218 (2017).

Speth, P, et al., "Cellular and plasma adriamycin concentrations in long-term infusion therapy of leukemia patients", Cancer Chemother Pharmacol 20, 305-310 (1987).

Speth, P, et al., "Clinical pharmacokinetics of doxorubicin", Clin Pharmacokine 15, 15-31 (1988).

Speth, P, et al., "Plasma and cellular Adriamycin concentrations in patients with myeloma treated with ninety-six-hour continuous infusion", Clin Pharmacol Ther 41, 661-665 (1987).

Stehle, G, et al., "Plasma protein (albumin) catabolism by the tumor itself—implications for tumor metabolism and the genesis of cachexia", Crit Rev Oncol Hematol 26, 77-100 (1997).

Tacar, O, et al., "Doxorubicin: an update on anticancer molecular action, toxicity and novel drug delivery systems", J Pharm Pharmacol 65, 157-170 (2013).

Tahover, E, et al., "Emerging delivery systems to reduce doxorubicin cardiotoxicity and improve therapeutic index: focus on liposomes", Anticancer Drugs 26, 241-258 (2015).

Van Der Meel, R, et al., "Cancer nanomedicines: oversold or underappreciated?", Expert Opin Drug Deliv 14, 1-5 (2017).

Von Hoff, D, et al., "Risk factors for doxorubicin-induced congestive heart failure", Ann Intern Med 91, 710-717 (1979).

Zensi, A, "Human serum albumin nanoparticles modified with apolipoprotein A-I cross the blood-brain barrier and enter the rodent brain", J Drug Target 18, 842-848 (2010).

Yu, C, et al., "Single Protein Encapsulated Doxorubicin as an Efficacious Anticancer Therapeutic", Adv Therap 3(11), 2000135, 19 pages (2020).

\* cited by examiner

SINGLE PROTEIN-ENCAPSULATED PHARMACEUTICS FOR ENHANCING THERAPEUTIC EFFECTS

CROSS REFERENCE TO RELATED APPLICATION

This application claims priority to U.S. Provisional Application No. 62/746,964, filed on Oct. 17, 2018. The entire content of this application is hereby incorporated by reference herein.

BACKGROUND

Chemotherapy is a type of cancer treatment that uses one or more anti-cancer drugs (chemotherapeutic agents) as part of a standardized chemotherapy regimen. It comes to connote non-specific usage of intracellular poisons to inhibit mitosis, cell division. The chemotherapeutic agents could be either cytotoxic or genotoxic or both. Chemotherapeutic techniques have a range of side-effects that depend on the type of medications used. The most common medications affect mainly the fast-dividing cells of the body, such as blood cells and the cells lining the mouth, stomach, and intestines. Chemotherapy-related toxicities can occur acutely after administration, within hours or days, or chronically, from weeks to years. In severe cases, chemotherapeutic agents can cause organ damages, such as cardiotoxicity (heart damage) by anthracycline drugs, hepatotoxicity (liver damage) by many cytotoxic drugs, nephrotoxicity (kidney damage) by tumor lysis syndrome and ototoxicity (damage to the inner ear) by platinum based rugs.

The small molecule anthracycline drug doxorubicin (DOX) is one of widely used anticancer therapeutic agents. Among the most potent FDA-approved chemotherapeutics, the anthracycline drug (Carvalho, C., et el., *Curr Med Chem*, 2009, 16, 3267-3285) displays a broad spectrum of antineoplastic activities against both solid and hematologic tumors (Tacar, O., S et el., *J Pharm Pharmacol*, 2013, 65, 157-170; Tahover, E., et el., *Anticancer Drugs*, 2015, 26, 241-258; and Shafei, A., et el., *Biomed Pharmacother*, 2017, 95, 1209-1218). However, as a small and hydrophobic molecule, DOX indiscriminately infiltrates all tissues and organs, causing systemic toxicities such as cardiomyopathy and myelosuppression. When DOX's cumulative dose reaches a certain level, incidents of congestive heart failure increase sharply (Von Hoff, D. D., et el., *Ann Intern Med*, 1979, 91, 710-717), which imposes a lifetime limit of <450 mg/m$^2$ for DOX treatment. DOX-induced cardiomyopathy may involve oxidative stress, contractile protein downregulation, and p53-induced apoptosis (Chatterjee, K., et el., *Cardiology*, 2010, 115, 155-162). Its antitumor potency is derived from the fact that DOX can easily penetrate cancer cell membranes and concentrate in the nucleus to effectively bind DNA and subsequently inhibit topoisomerases, DNA replication and transcription. At the same time, these properties also enable DOX to rapidly enter healthy cells in contact on its path, causing serious damage to healthy organs and tissues. In addition, DOX displays poor pharmacokinetics (PK) that can be described by either biphasic (Greene, R. F., et el., *Cancer Res*, 1983, 43, 3417-3421; Speth, P. A., Linssen, et el., *Cancer Chemother Pharmacol*, 1987, 20, 305-310; and Speth, P. A., et el., *Clin Pharmacol Ther*, 1987, 41, 661-665) or triphasic curves (Benjamin, R. S., et el., *Cancer Res*, 1977, 37, 1416-1420; and Eksborg, S., et el., *Eur J Clin Pharmacol*, 1985, 28, 205-212) with a short plasma circulation half-life of 5-12 minutes and a terminal phase half-life of about 30 hours (Speth, P. A., et el., *Clin Pharmacokine*, 1988, t 15, 15-31). These undesirable characteristics severely impact the clinical outcome of DOX treatment due to its narrow therapeutic window.

Various efforts and studies have been undertaken to reduce DOX's toxicities. The key to success is to limit DOX's access to normal cells while increasing its traffic/delivery to tumors, which in principle may be achieved by a rationally designed strategy of associating/binding/complexing/conjugating DOX with a macromolecular, self-assembled, or aggregated system with MW above the renal clearance of about 50 kD. By associating DOX with a nano-sized moiety, such a system significantly improves the PK of DOX, dramatically increases its circulation lifetime, and enhances its access/delivery to tumors via the enhanced permeability and retention (EPR) effect due to tumors' irregular neovasculature and poor lymphatic drainage. Numerous studies with liposomes, polymer conjugation, protein conjugation, protein nanoparticles and metal/inorganic nanoparticles (NPs) have consistently demonstrated these underlying principles. However, current systems have seen limited success, which is true even with FDA-approved Doxil (Petersen, G. H., et el., *J Control Release*, 2016, 232, 255-264). There are a number of reasons as to why current systems do not live up to their expectations. Liposomes fuse nonspecifically with cell membranes to unload the cargo DOX, causing systemic toxicities. Chemically conjugating DOX to synthetic polymers and proteins modifies DOX to allow conjugation, but at the same time faces the challenge of its controlled release and changed properties due to chemical modifications. While metal/inorganic NPs were once hailed as the silver bullets for efficient drug delivery, they are far from natural systems. There is still not a good understanding of their interactions with tissues and organs. Furthermore, many of these non-natural systems may be recognized by our body's sophisticated immune system, leading to a broad range of responses that may vary among different patients. Lastly, there is a limited knowledge as to how the human body disposes an artificial system (synthetic polymer, metal/inorganic NPs, etc). While proteins and amide-based polymers may be enzymatically degraded to monomers that can be used/processed by metabolism, it is unclear what the long term effects are with non-biodegradable polymers and metal/inorganic NPs. Although human serum albumin nanoparticles (HSA-NPs) can have different forms with varying sizes and chemical conjugation/cross-linking, they all differ significantly from free HSA (Kratz, F., *J Control Release*, 2008, 132, 171-183; Sebak, S., et el., *Int J Nanomedicine*, 2010, 5, 525-532; Zensi, A., *J Drug Target*, 2010, 18, 842-848; Abbasi, S., *J Drug Deliv* 2012, 686108; Elzoghby, A. O., et el., *J Control Release*, 2012, 157, 168-182; Jin, G., et el., *Oncol Rep*, 2012, 36, 871-876; Lomis, N., et el., *Nanomaterials*, 2016, (Basel) 6; and Nateghian, N., et el., *Chem Biol Drug Des*, 2016, 87, 69-82). Consequently, their circulation PK, interaction with host organs/tissues/cells, and potential elicitation of immune responses can be considerably different from those of natural HSA. All these issues directly contribute to the limited success with current cancer drug formulation/delivery systems (Petersen, G. H., et el., *J Control Release*, 2016, 232, 255-264; van der Meel, et el., *Expert Opin Drug Deliv*, 2017, 14, 1-5; and Mukherjee, A., et el., 1996, All About Albumin: Biochemistry, Genetics and Medical Applications. San Diego, Calif.: Academic Press Limited). Thus, there is an urgent need for formulations that not only reduce the toxicity, but also enhance efficacy in human clinical settings for DOX and other anticancer drugs.

HSA is the most abundant serum protein in the body, with a total of about 460 g distributing among the blood circulation, the lymphatic system and the extracellular/intracellular compartments (Peters. T., 1996, All About Albumin: Biochemistry, Genetics and Medical Applications. San Diego, Calif.: Academic Press Limited). Its functions include providing essential colloidal osmotic pressure, balancing plasma pH, and binding and transporting hydrophobic molecules such as fatty acids and bilirubin. HSA possesses some unique properties (Hoogenboezem, E. N., and Duvall, C. L., *Adv Drug Deliv Rev*, 2018, 130, 73-89): 1) being highly soluble and thermally stable, 2) capable of binding a variety of ligands with different binding affinity, 3) being endocytosed and transcytosed into and cross cells via receptors, 4) displaying an unusually long half-life of 19 days due to effective endosome recycling by the neonatal Fc receptor (FcRn) and rescue from renal clearance via Megalin/Cubilin-complexes (Chaudhury, C., *J Exp Med*, 2003, 197, 315-322; Anderson, C. L., et al., *Trends Immunol*, 2006, 27, 343-348; Chaudhury, C., et al., *Biochemistry*, 2006, 45, 4983-4990; and Kim, J., Bronson, et al., *Am J Physiol Gastrointest Liver Physiol*, 2006, 290, G352-360), 5) able to accumulate at tumor tissues due to EPR effects, and 6) being preferentially taken up and metabolized by cancer cells to serve as nutrients (Stehle, G., et al., *Crit Rev Oncol Hematol*, 1997, 26, 77-100; Commisso, C., et al., *Nature*, 2013, 497, 633-637; and Kamphorst, J. J., et al., *Cancer Res*, 2015, 75, 544-553).

SUMMARY

Applicant has identified a method to tightly bind therapeutic agents (e.g. doxorubicin) within single proteins (e.g. albumin), while substantially maintaining the properties of the single protein. This method provides new compositions having lower toxicity and/or wider therapeutic windows.

In one embodiment, the invention provides a composition comprising a single protein having one or more molecules of a pharmaceutical agent tightly bound therein.

The invention also provides a method to treat cancer in an animal comprising administering to the animal a composition that comprises a single protein having one or more molecules of an anti-cancer agent tightly bound therein.

The invention also provides a method to treat a bacterial or fungal infection in an animal comprising administering to the animal a composition that comprises a single protein having one or more molecules of an antibacterial or antifungal agent tightly bound therein.

The invention also provides a method comprising: a) combining a first solution that comprises a pharmaceutical agent with a second solution that comprises a single protein, water, and a polar organic solvent to provide a third solution; and b) stirring the third solution under conditions that allow one or more molecules of the pharmaceutical agent to become tightly bound within each single protein molecule. The invention also provides a composition prepared by a method of the invention.

The invention also provides a pharmaceutical composition that comprises 1) a single protein with one or more molecules of a pharmaceutical agent tightly bound therein and 2) a pharmaceutically acceptable carrier.

The invention also provides a composition as described herein for the prophylactic or therapeutic treatment of cancer.

The invention also provides the use of a composition as described herein to prepare a medicament for treating cancer in an animal.

The invention also provides a composition as described herein for the prophylactic or therapeutic treatment of a bacterial infection.

The invention also provides the use of a composition as described herein to prepare a medicament for treating a bacterial infection in an animal.

DETAILED DESCRIPTION

Figure 30:
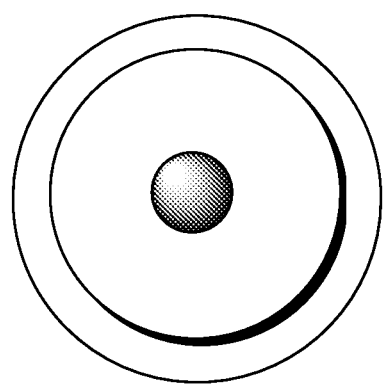
FIG. 30: HSA-fully encapsulated pharmaceuticals.
Figure 31:
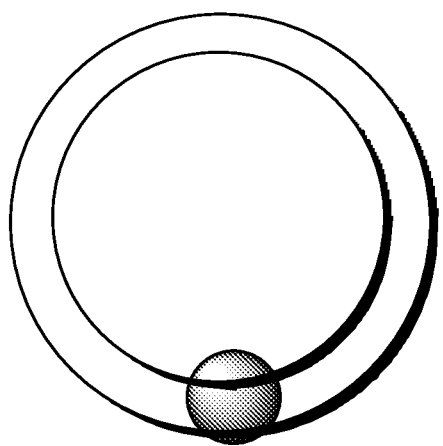
FIG. 31: HSA-partially encapsulated pharmaceuticals.

In one embodiment, the invention provides a composition comprising a single protein having one or more molecules of a pharmaceutical agent "tightly bound" therein. As used herein, the term "tightly bound" means that the molecule of the pharmaceutical agent is encapsulated within the single protein; the pharmaceutical agent is not covalently bounded to the single protein either directly or through an intervening group. In one embodiment, the molecule of the pharmaceutical agent is completely encapsulated by the single protein (FIG. 30). In another embodiment, only part of the surface area of the molecule of the pharmaceutical agent is encapsulated by the single protein (See FIG. 31). In another embodiment, one or more molecules of the pharmaceutical agent may be completely encapsulated by the single protein and one or more molecules of the pharmaceutical agent may only have part of its surface area encapsulated by the single protein.

As used herein, the term "single protein" includes a single molecular species of a protein of both natural and synthetic origins, including proteins isolated from both living organisms and bioengineered systems. Furthermore, the protein may contain other non-protein components through either covalent linkage or noncovalent interaction. In one embodiment, the term does not include multimolecular species of a protein, such as a dimer, trimer, oligomer, or multimer. In one embodiment, the single protein is an albumin, a globulin, a fibrinogen, IgA, IgM IgG, or another human protein.

As used herein, the term "albumin" includes any albumin. In one embodiment, the albumin is mammalian. In one embodiment, the albumin is human, cow, sheep, horse, or pig albumin. In one embodiment, albumin is non-mammalian. In one embodiment, the albumin is prepared from recombinant techniques. In the compositions of the invention, the albumin is not present in the form of particles, e.g. a nano-particle. Accordingly, the tightly-bound molecules of the pharmaceutical agent are encapsulated in pockets within the albumin structure, not within pores of an albumin nanoparticle.

As used herein, the term "globulin" includes any globulin. Globulins are a heterogeneous group of large serum proteins, not including albumin, which are soluble in salt solutions. There are three principal subsets of globulins, which are distinguished by their respective degrees of electrophoretic mobility: alpha globulin, beta globulin, and gamma globulin. Non-limiting examples of various globulins include clotting proteins, complement, many acute phase proteins, immunoglobulins (Igs), and lipoproteins. In one embodiment, the globulin is mammalian. In one embodiment, the globulin is human, cow, sheep, horse or pig albumin. In one embodiment, globulin is non-mammalian. In one embodiment, the globulin is recombinant globulin. In one embodiment, the globulin is an immunoglobulin (Ig), such as an IgA, IgM, IgG, IgE or IgD antibody.

As used herein, the term "antibody" includes a single-chain variable fragment (scFv or "nanobody"), humanized, fully human or chimeric antibodies, single-chain antibodies, diabodies, and antigen-binding fragments of antibodies that do not contain the Fc region (e.g., Fab fragments). In certain embodiments, the antibody is a human antibody or a humanized antibody. A "humanized" antibody contains only the three CDRs (complementarity determining regions) and sometimes a few carefully selected "framework" residues (the non-CDR portions of the variable regions) from each donor antibody variable region recombinantly linked onto the corresponding frameworks and constant regions of a human antibody sequence. A "fully humanized antibody" is created in a hybridoma from mice genetically engineered to have only human-derived antibody genes or by selection from a phage-display library of human-derived antibody genes.

As used herein, the term "fibrinogen" includes any fibrinogen. Fibrinogen is a soluble glycoprotein present in blood plasma, from which fibrin is produced by the action of the enzyme thrombin. In one embodiment, the fibrinogen is mammalian. In one embodiment, the fibrinogen is human, cow, sheep, horse, or pig fibrinogen. In one embodiment, fibrinogen is non-mammalian. In one embodiment, the fibrinogen is a recombinant fibrinogen.

As used herein, the term "polar organic solvent" includes solvents that are miscible with water or partially dissolved in water. For example, the term includes water miscible solvents or water partially dissolved solvents. The term "polar organic solvent" includes:

(1) Water soluble alcohols: methanol, ethanol, isopropanol, butanol, pentanol, t-butanols, etc
(2) Water soluble diols and triols, tetraols: ethylene glycol, propylene glycol, glycerol, etc
(3) Water soluble aldehydes and ketones: acetone, butanone, pentanones, hexanones, acetaldehyde, formyl aldehyde, propionaldehyde, butyraldehyde, etc
(4) Water soluble nitriles: acetonitrile, propionitrile, butanitrile, etc
(5) Water soluble polymers with low molecular weight: polyethylene glycols, polypropylene glycols, etc
(6) Water soluble amides: DMF, dimethylacetamide, dimethylpropanamide, etc,
(7) Water soluble ethers: diethyl ether, THF, dioxanes, etc
(8) All Other water soluble organic solvents: DMSO, etc As used herein, the term "pharmaceutical agent" includes any pharmaceutically active agent that can be tightly bound within the single protein. In one embodiment, the pharmaceutical agent is hydrophobic. In one embodiment, the pharmaceutical agent is water soluble at the desired pH values. In one embodiment, the pharmaceutical agent is an anticancer agent, an antiinflammatory agent, a CNS agent, an antifungal agent, or an antibiotic agent. In one embodiment, the pharmaceutical agent is an anti-cancer compound. In one embodiment, the pharmaceutical agent is doxorubicin. In particular, the pharmaceutical agent is water soluble at a pH from about −4 to about 20. In one embodiment the pharmaceutical agent is water soluble at a pH from about 0 to about 14. In one embodiment the pharmaceutical agent has limited water solubility at any pH values. In one embodiment the pharmaceutical agent is doxorubicin, epirubicin, mitoxantrone, daunorubicin, vincristine, vinorelbine, vinblastine, topotecan, irinotecan, actinomycin D, idarubicin, methotrexate, pemetrexed, raltitrexed, SN-38, ixabepilone, eribulin, vindesine, camptothecin, paclitaxel, docetaxel, bendamustine, nelarabine, pirarubicin, clofarabine, valrubicin, chlorambucil, etc. In one embodiment, the pharmaceutical agent comprises an amino group or amino groups. In one embodiment, the pharmaceutical agent comprises a carboxyl acid group or carboxyl acid groups. In one embodiment, the pharmaceutical agent comprises carboxyl acid group(s) and one amino group. In one embodiment the pharmaceutical agent is an antibiotic agent. In one embodiment the pharmaceutical agent is amphotericin B, clofazimine, rifampicin, chloramphenicol, tetracycline, or a fluoroquinolone antibiotic.

As used herein, the term "second pharmaceutical agent" includes any pharmaceutically active agent. In one embodiment, the second pharmaceutical agent can be tightly bound within the single protein. In one embodiment, the second pharmaceutical agent is hydrophobic. In one embodiment, the second pharmaceutical agent is water soluble at the desired pH values. In one embodiment, the second pharmaceutical agent is an anticancer agent, an antiinflammatory agent, a CNS agent, an antifungal agent, or an antibiotic agent. In one embodiment, the pharmaceutical agent is an anti-cancer compound. In one embodiment, the second pharmaceutical agent is doxorubicin. In one embodiment, the second pharmaceutical agent is docetaxel. In particular, the second pharmaceutical agent is water soluble at a pH from about −4 to about 20. In one embodiment the second pharmaceutical agent is water soluble at a pH from about 0 to about 14. In one embodiment the second pharmaceutical agent has limited water solubility at any pH values. In one embodiment the second pharmaceutical agent is doxorubicin, epirubicin, mitoxantrone, daunorubicin, vincristine, vinorelbine, vinblastine, topotecan, irinotecan, actinomycin D, idarubicin, methotrexate, pemetrexed, raltitrexed, SN-38, ixabepilone, eribulin, vindesine, camptothecin, paclitaxel, docetaxel, bendamustine, nelarabine, pirarubicin, clofarabine, valrubicin, chlorambucil, etc. In one embodiment, the second pharmaceutical agent comprises an amino group or amino groups. In one embodiment, the second pharmaceutical agent comprises a carboxyl acid group or carboxyl acid groups. In one embodiment, the second pharmaceutical agent comprises carboxyl acid group(s) and one amino group. In one embodiment the second pharmaceutical agent is an antibiotic agent. In one embodiment the second pharmaceutical agent is amphotericin B, or clofazimine, or rifampicin, chloramphenicol, or tetracycline, or fluoroquinolone antibiotics.

Figure 9:
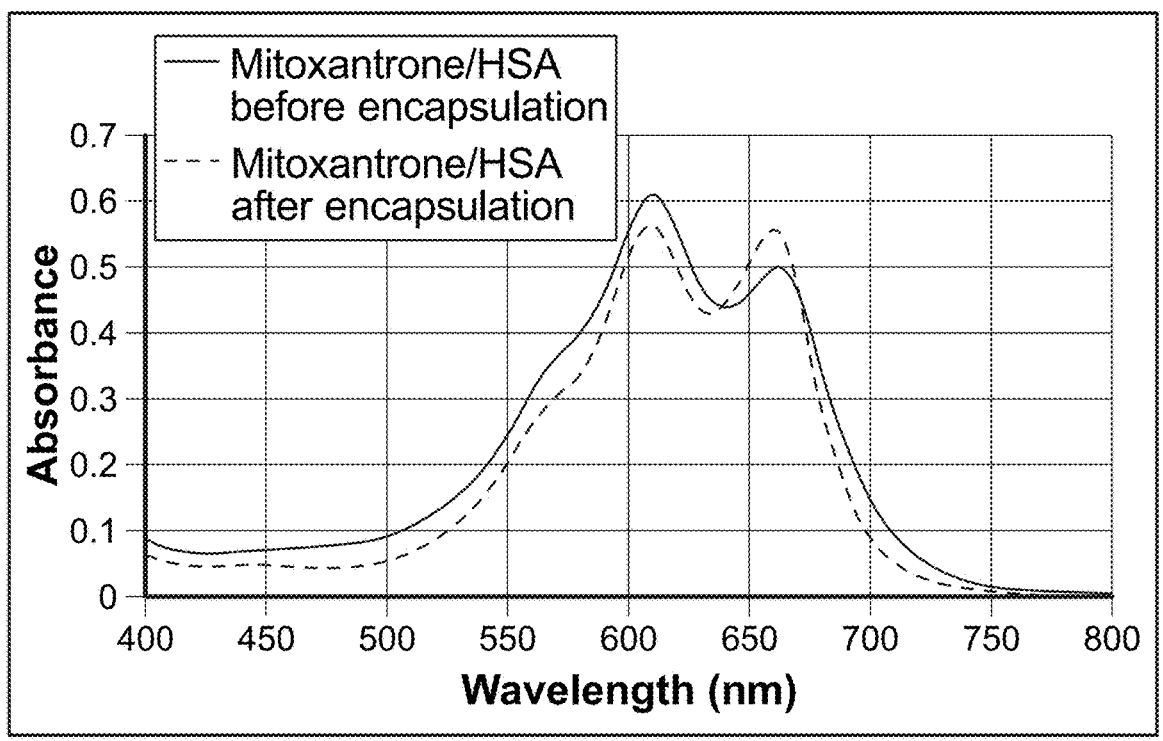
FIG. 9: Mitoxantrone's spectral changes before and after encapsulation in PBS (pH=7.4), see Example 7.
Figure 11:
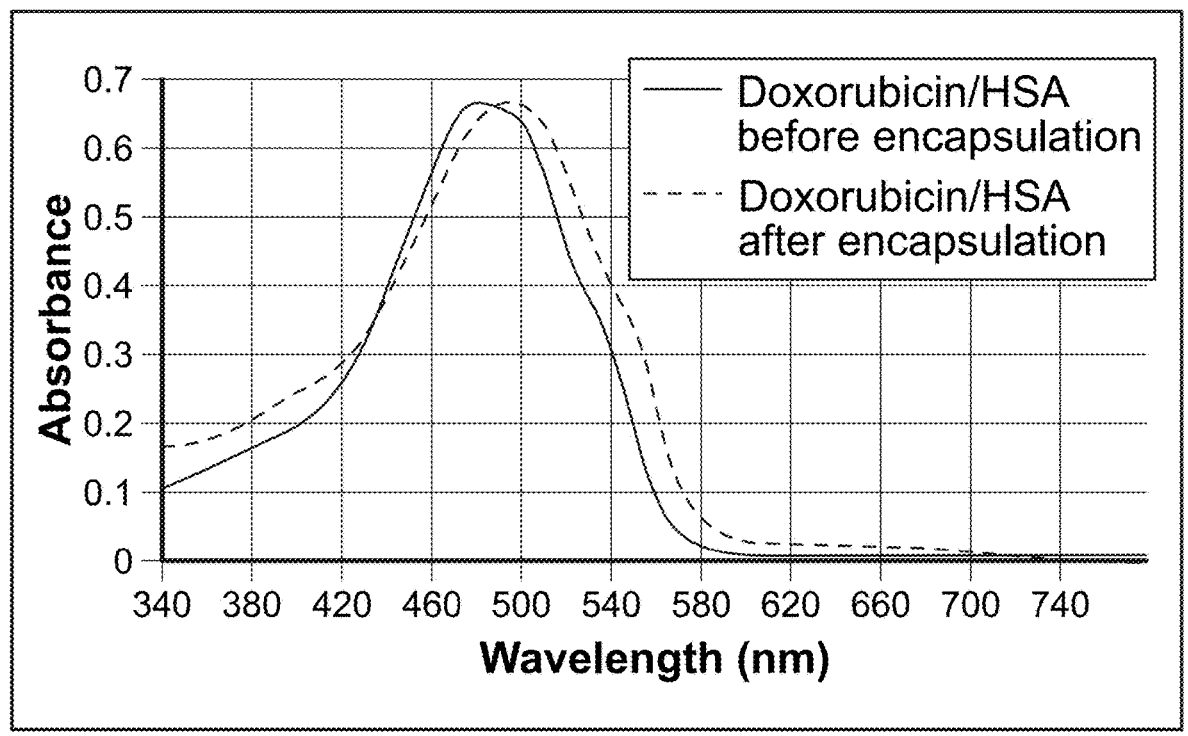
FIG. 11: Doxorubicin's UV spectral Changes before and after encapsulation in PBS (pH=7.4), see Example 8.
Figure 13:
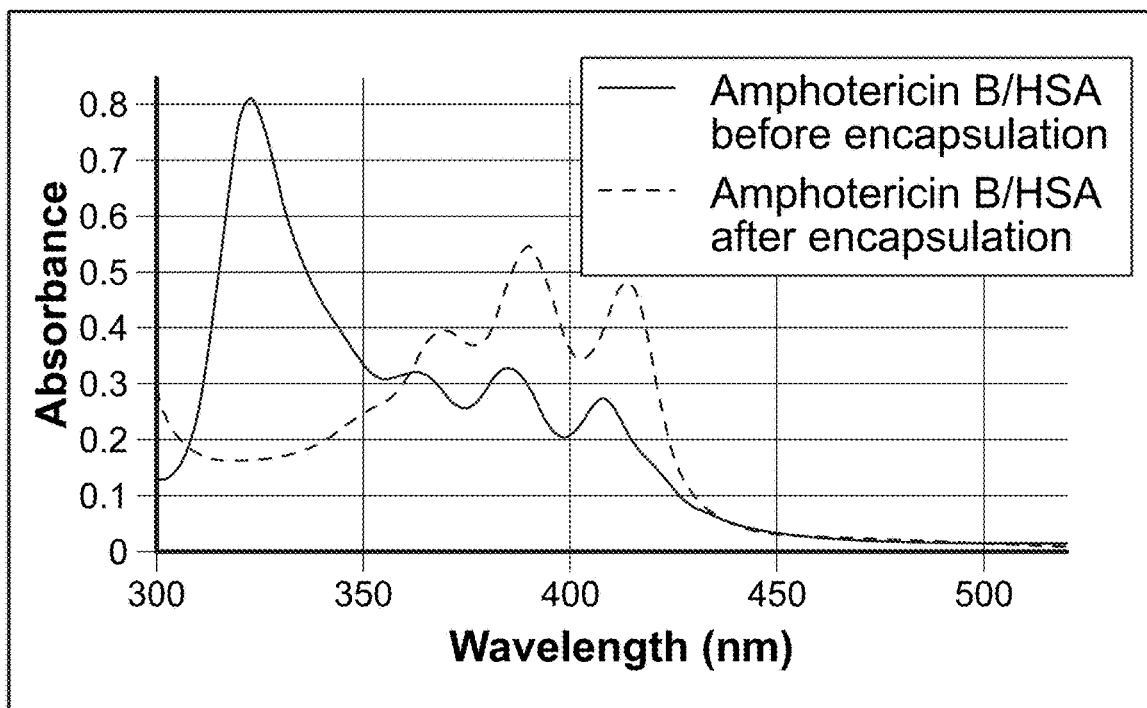
FIG. 13: Amphotericin B's spectral changes before and after encapsulation in PBS (pH=7.4), see Example 8.
Figure 15:
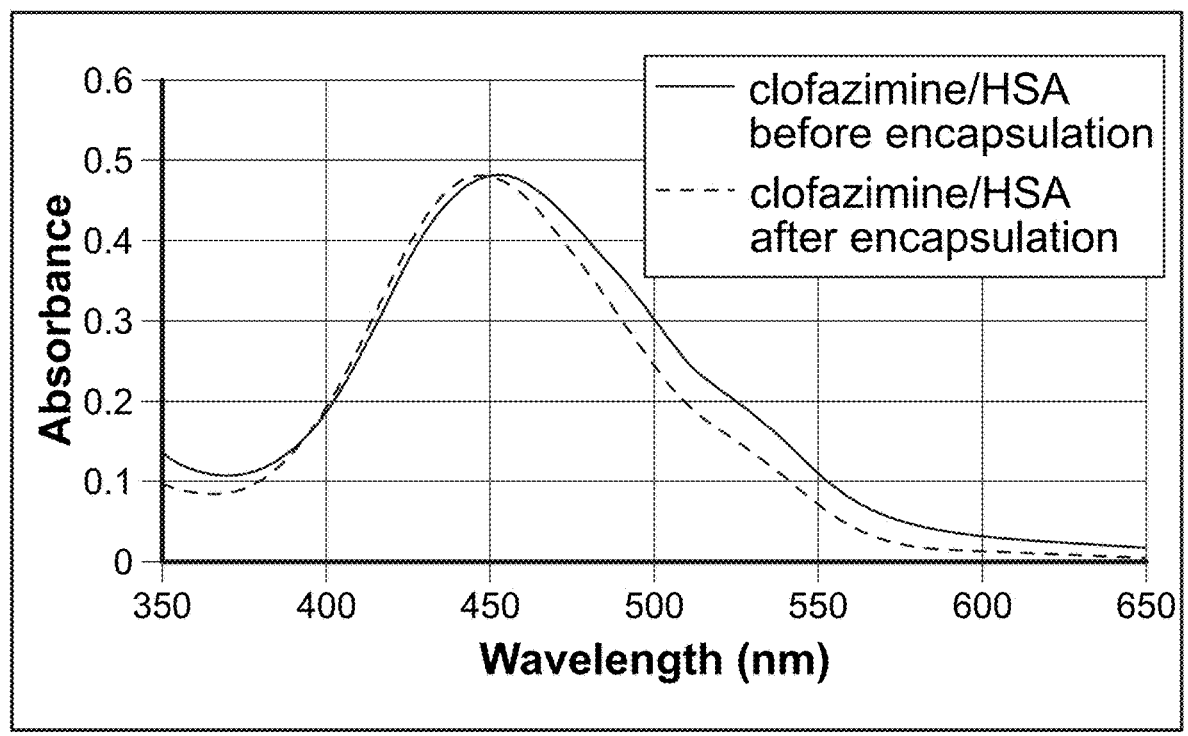
FIG. 15: Clofazimine's spectral changes before and after encapsulation in PBS (pH=7.4), see Example 10.
Figure 29:
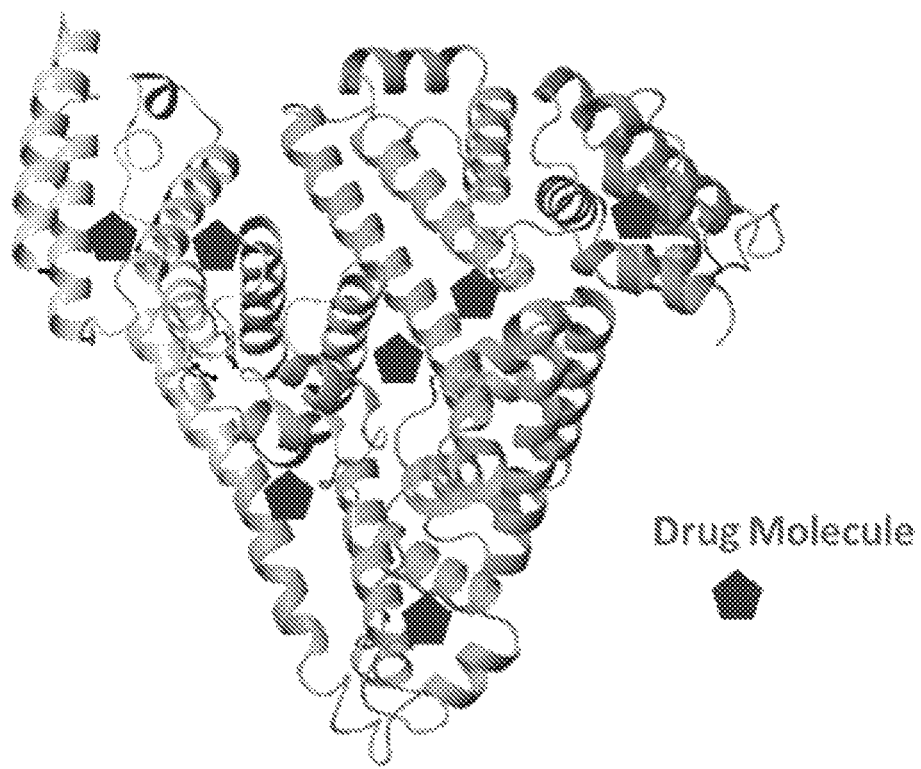
FIG. 29: Diagram of Albumin-encapsulated Pharmaceuticals (drug molecules).

HSA is well-known for its conformation changes when its environment is altered. It has been reported that HSA displayed different confirmations in acidic, neutral and basic conditions. HSA's conformation in a cosolvent, such as ethanol/water, or methanol/ethanol/water, or 1, 4-dioxane/water, or 2-butanone/ethanol/water, or acetone/water, or DMSO/water, or other organic solvents/water mixtures is dramatically different from the pure water (Borisover, M. D., et el., *Thermochimica Acta,* 1996, 284, 263-277). The literature shows that suspending HSA in the water/organic coso vents is accompanied by two main processes, (1) the water desorption-sorption, (2) the non-sorption that is attributed to rupture of protein-protein contact, depending on the nature of organic solvent and water content. Furthermore, the prepared HSA solution in the water/organic cosolvents results in the increase in the accessible surface areas, which has capacity to change the water sorption and calorific properties of the intended HSA suspension. HSA in the water/organic cosolvents is no longer in its natural state; it is partially denatured. Due to the fact that relative polarity of the cosolvent is lower than the pure water's, the resulting conformation changes of HSA in the desired organics/water mixture would allow some of the hydrophobic pockets to be opened up, allowing pharmaceuticals agents to be tightly bound or encapsulated into these hydrophobic pockets, see FIG. 29. For example, in Composition 7 below, multiple molecules of DOX are tightly bound inside each HSA molecule. In literature reports (Khan, S. N., et el., *Eur J Pharm Sci,* 2008, 35, 371-382; and Agudelo, D., et el., *PLoS One,* 2012, 7, e43814) wherein DOX and mitoxantrone were reversibly associated to human serum albumin (HSA), only 1 molecule of DOX or mitoxantrone was reported to be associated with each HSA. Additionally, the UV spectra of the reversibly associated DOX and mitoxantrone showed no change from the corresponding unassociated materials. In this invention, once doxorubicin or mitroxantrone was encapsulated into a HSA molecules, a red-shifting of UV spectra for doxorubicin or mitroxatrone was observed, See FIG. 11 for composition 7 and FIG. 9 for composition 6. In some case, once being capsulated into HSA molecule, an absorbance band of drug molecules is eliminated, see FIG. 13 for composition 8 where an absorption at 324 nm of amphotericin B is completely eliminated one being encapsulated inside HSA molecule. In other case, the blue-shifting of UV spectra of certain drug molecules after being capsulated into a HSA molecule was observed and recorded, see FIG. 15 for composition 9, where clofazimine was encapsulated into a HSA molecule. The compositions of the invention that have pharmaceutical agent molecules tightly bound within albumin have novel properties, such as, for example, enhanced therapeutic effects.

In one embodiment, the single protein is dissolved in a co-solvents containing at least one water soluble organic solvent that helps the pharmaceutical agent to be able for being encapsulated into the single protein. The encapsulation process is monitored by UV or other instruments. Once the desired percent of single protein-encapsulated pharmaceuticals is achieved, the encapsulation process is terminated and the final product is prepared. After the filtration (e.g. through 0.22 um membrane or high speed centrifugation or other sterilization procedure), the concentrations of pharmaceuticals can be quantified by UV spectrometer, HPLC or other methods after organic solvent extraction through the proteins precipitation. After quantification, the single protein-encapsulated pharmaceuticals solutions can be frozen at −20° C. or lyophilized to powder products. In addition, in some embodiments, the single protein-encapsulated pharmaceuticals can be further purified via running through Sephadex G25 column, in which the large molecule, single protein-encapsulated pharmaceuticals come out the first, followed by the un-capsulated pharmaceuticals. In some embodiments, the single protein-encapsulated pharmaceuticals can be further purified via dialysis using the dialysis pouch with different molecular weight cutoffs, in which the un-capsulated pharmaceuticals with small molecular weights will be dialyzed out and the single protein-encapsulated pharmaceuticals with macular weights >20 kd will be kept inside the dialysis bag. This invention provides novel method to prepare single protein-encapsulated pharmaceuticals without chemically modifying structures of the single protein or the intended pharmaceuticals.

Figure 5:
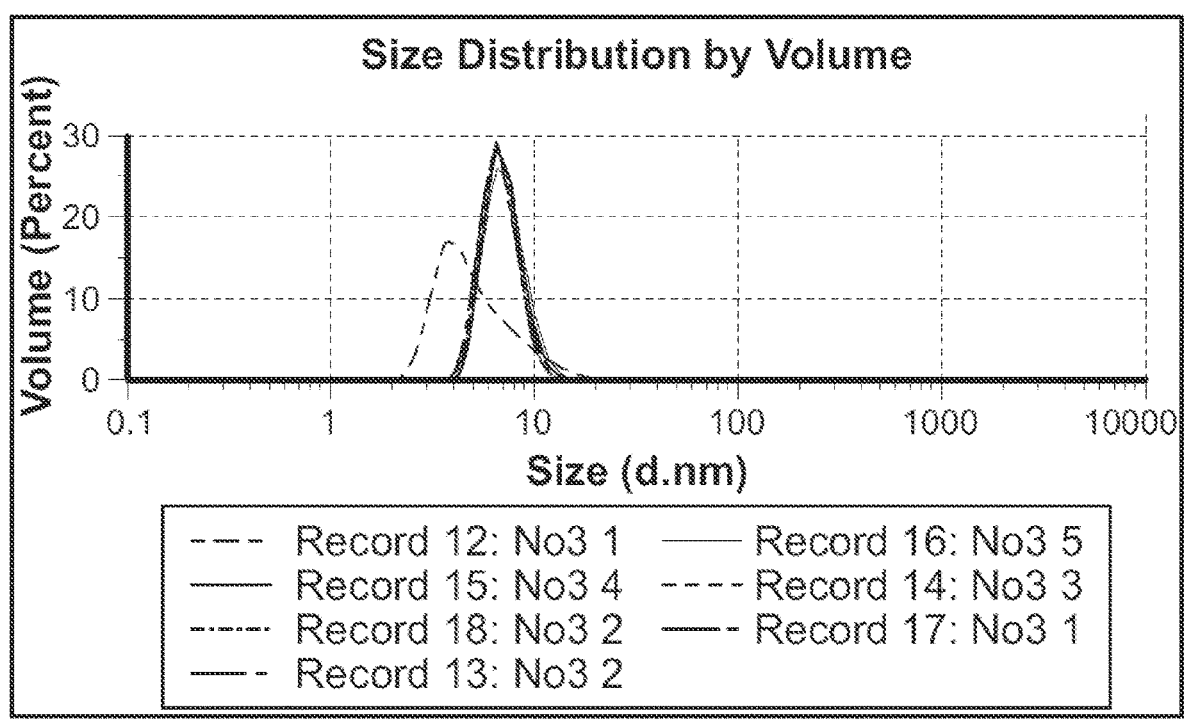
FIG. 5: HSA-encapsulated idarubicin particle size distribution by DLS, see Example 3.
Figure 8:
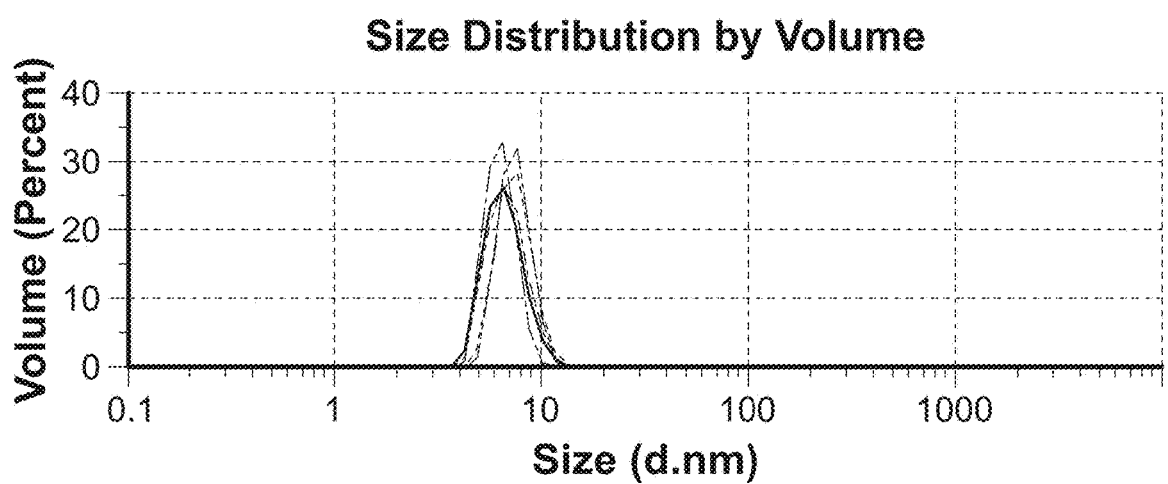
FIG. 8: HSA-encapsulated daunorubicin particle size distribution by DLS, see Example 6.
Figure 10:
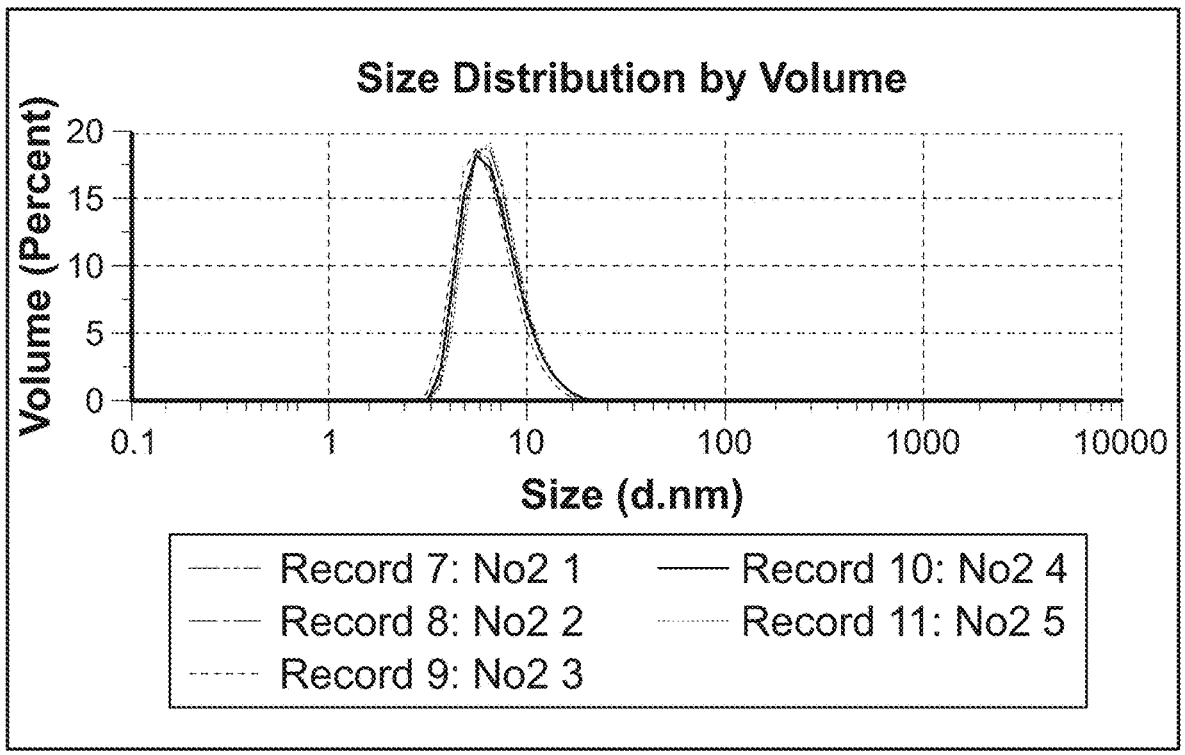
FIG. 10: HSA-encapsulated mitoxantrone particle size distribution by DLS, see Example 7.
Figure 12:
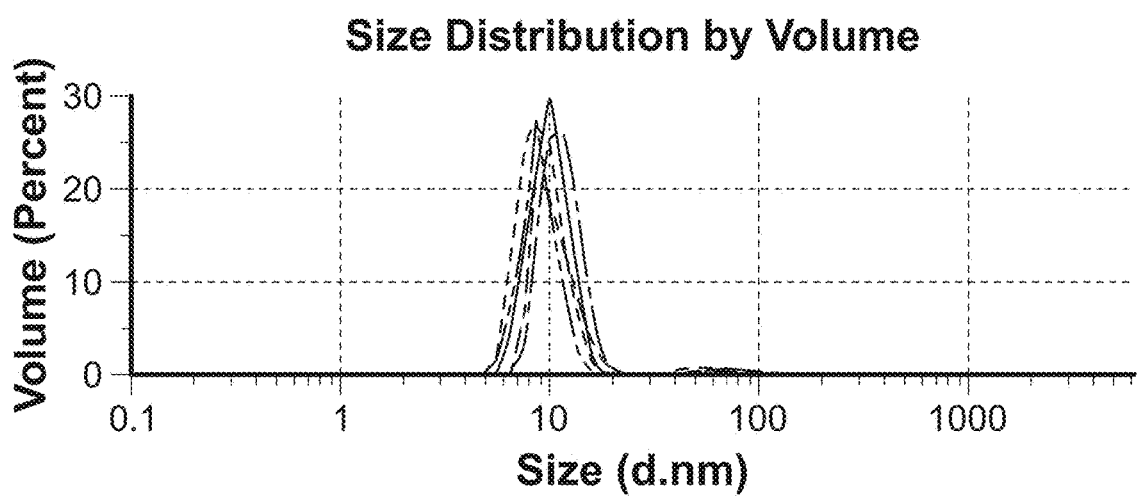
FIG. 12: HSA-encapsulated doxorubicin particle size distribution by DLS, see Example 8.
Figure 14:
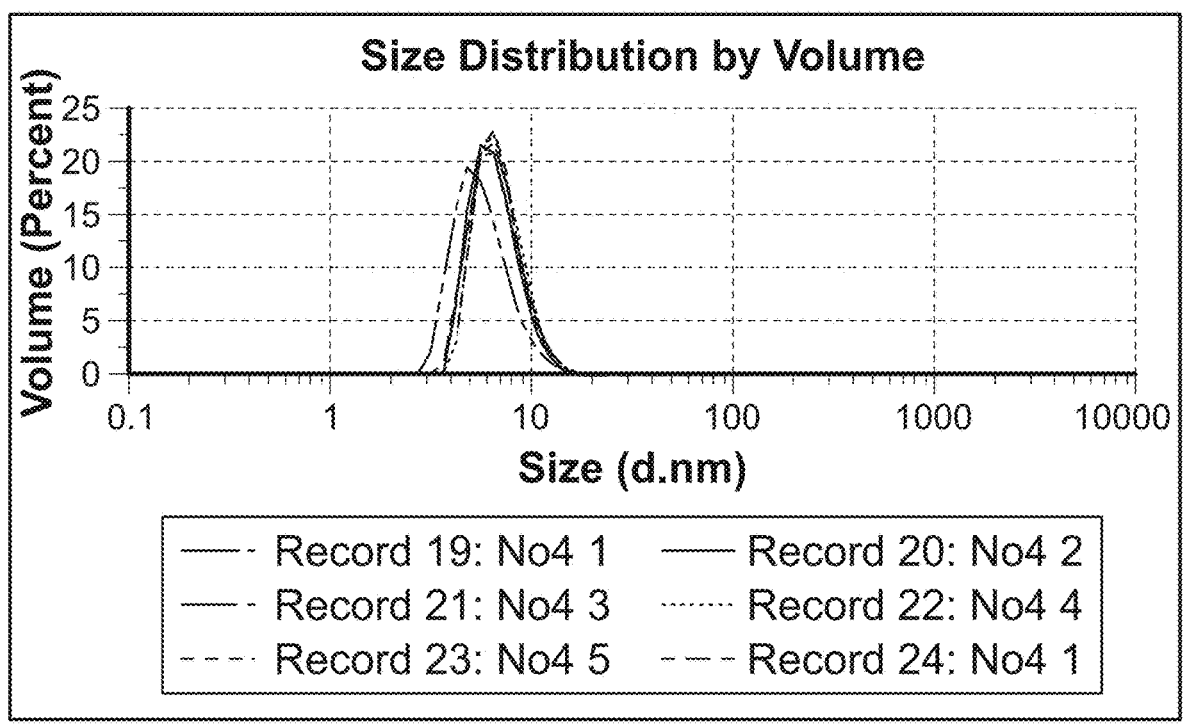
FIG. 14: HSA-encapsulated amphotericin B particle size distribution by DLS, see Example 8.
Figure 17:
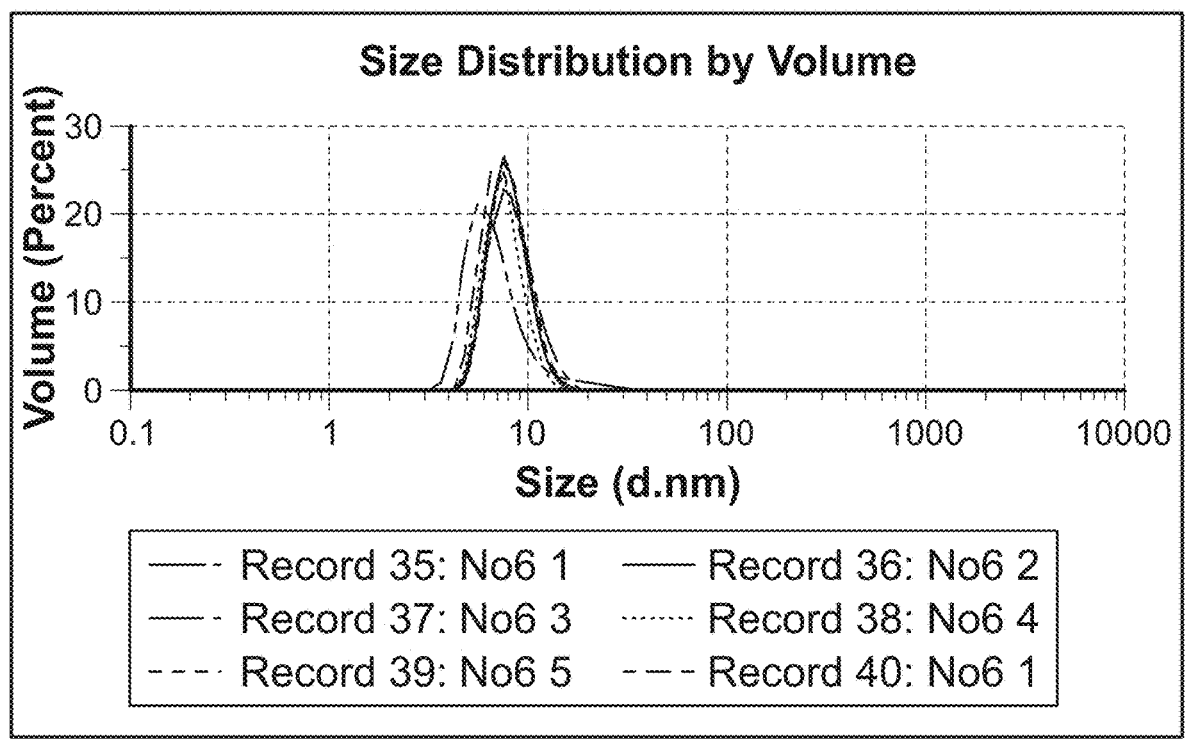
FIG. 17: HSA-encapsulated methotrexate particle size distribution by DLS, see Example 11.
Figure 32:
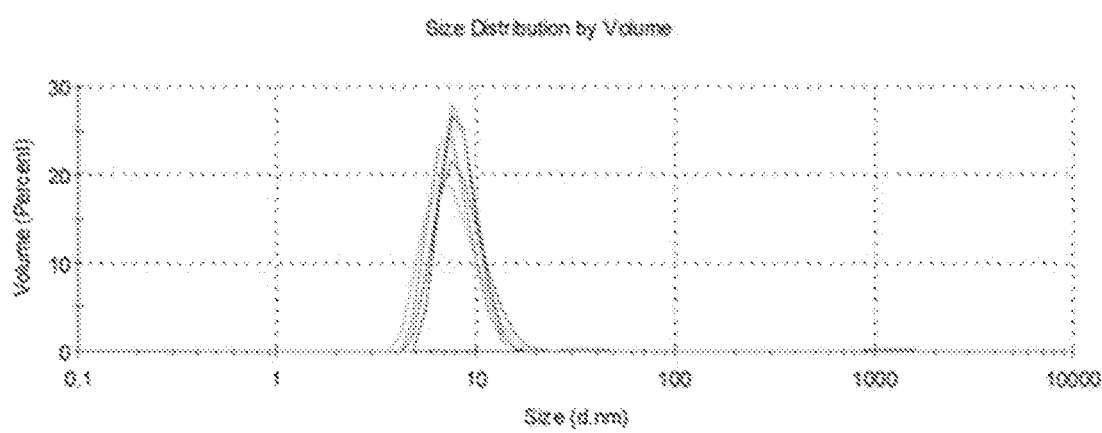
FIG. 32: HSA particle size distribution by DLS.

HSA is a biopolymer, with a molecular weight at about 66,000 g/mole with a particle size at about 10 nm (FIG. 32) determined by dynamic light scattering (DLS). In the compositions of the invention the particle size of the albumin having one or more molecules of a pharmaceutical agent encapsulated therein does not change, see FIG. 5 for composition 3, FIG. 8 for composition 5, FIG. 10 for composition 6, FIG. 12 for composition 7, FIG. 14 for composition 8, and FIG. 17 for composition 10. In one embodiment the albumin having one or more molecules of a pharmaceutical agent tightly bound therein is soluble in water. In another embodiment the albumin having one or more molecules of a pharmaceutical agent encapsulated therein is soluble in water at a pH in the range of from about 6 to about 8.

If the pharmaceutical agent is an anticancer agent, the composition comprising a single protein having one or more molecules of the pharmaceutical agent encapsulated therein may increase the MTD of the agent, because the encapsulated molecules prefer to go to the cancer cells and will have fewer interactions with the normal cells. If the pharmaceutical agent is an antibiotic, the composition comprising the single protein having one or more molecules of the pharmaceutical agent tightly bound therein may decrease the MIC (minimum inhibitory concentrations) against the microorganism, because the tightly-bound molecules favorably bind to the surface of both bacteria (gram-positive and gram-negative) and fungi. Therefore, in some embodiments the single protein-tightly bound pharmaceuticals can be characterized by the comparison of their MTD or MIC to that of free form of molecules.

As described in the previous section, during the preparation process, the intended pharmaceutical molecules are entrapped in the binding pockets of the single protein once the single protein-tightly bound pharmaceuticals are successfully prepared. Compared to the free form, the encapsulated molecules are surrounded by different environments, which could cause the changes of their UV spectra or florescence emission spectroscopy. The carrier, binding and proximity relationships of the encapsulated molecules can be characterized and analyzed using absorption, fluorescence, FTIR, or circular dichroism.

Single Protein Encapsulation can be particularly useful with pharmaceutical agents that have limited solubility. For example, Single Protein Encapsulation can be useful with a pharmaceutical agent that needs to be formulated with one or more surfactants or solubilizing carriers to facilitate administration. In many cases, surfactants and solubilizing carriers have undesirable properties that produce unwanted effects upon administration. Encapsulating a pharmaceutical agent that has limited solubility in a Single Protein can provide an administrable form of the therapeutic agent that does not include undesirable surfactants or solubilizing carriers. Accordingly, in one embodiment, the first pharmaceutical agent and/or the second pharmaceutical agent is an agent that has poor solubility (e.g. a solubility of less than about 0.1 µg/mL in water). In another embodiment, the pharmaceutical composition described herein does not comprise a surfactant or a solubilizing carrier.

In one embodiment, the pharmaceutical agent is an Anthracycline, a Cytoskeletal disruptor, an Inhibitor of topoisomerase I, an Inhibitor of topoisomerase II, a Kinase inhibitor, or a Vinca alkaloid or a derivative thereof.

In one embodiment, the second pharmaceutical agent is an Anthracycline, a Cytoskeletal disruptor, an Inhibitor of topoisomerase I, an Inhibitor of topoisomerase II, a Kinase inhibitor, or a Vinca alkaloid or a derivative thereof.

In one embodiment, the pharmaceutical agent is an Anthracycline and the second pharmaceutical agent is a Cytoskeletal disruptor.

In one embodiment, the pharmaceutical agent is an Anthracycline and the second pharmaceutical agent is a Vinca alkaloid or a derivative thereof.

In one embodiment, the pharmaceutical agent is a Cytoskeletal disruptor and the second pharmaceutical agent is an Inhibitor of topoisomerase I.

In one embodiment, the pharmaceutical agent is a Cytoskeletal disruptor and the second pharmaceutical agent is an I Inhibitor of topoisomerase II.

In one embodiment, the pharmaceutical agent is an Anthracycline and the second pharmaceutical agent is a kinase inhibitor.

In one embodiment, the pharmaceutical agent is an Alkylating agent, an Antimetabolite, an Anti-microtubule agent, a Topoisomerase inhibitors, or a Cytotoxic antibiotic.

In one embodiment, the second pharmaceutical agent is an Alkylating agent, an Antimetabolite, an Anti-microtubule agent, a Topoisomerase inhibitors, or a Cytotoxic antibiotic.

In one embodiment, the pharmaceutical agent is an Anti-microtubule agent and the second pharmaceutical agent is a Topoisomerase inhibitor.

In one embodiment, the pharmaceutical agent is an Anti-microtubule agent and the second pharmaceutical agent is a Cytotoxic antibiotic.

In one embodiment, the pharmaceutical agent is a Topoisomerase inhibitor and the second pharmaceutical agent is a Cytotoxic antibiotic.

In one embodiment, the pharmaceutical agent is an Anti-microtubule agent and the second pharmaceutical agent is an alkylating agent.

In one embodiment, a plurality of molecules of the pharmaceutical agent are tightly bound within each single protein.

In one embodiment, at least one molecule of the pharmaceutical agent is tightly bound within each single protein.

In one embodiment, the composition comprises water and one or more water soluble organic solvents.

In one embodiment, the pharmaceutical agent has poor water solubility.

In one embodiment, the maximum tolerated dose of the pharmaceutical agent in the composition is greater than the maximum tolerated dose of the free form of pharmaceutical agent alone (e.g. formulated without the single protein).

In one embodiment, the maximum tolerated dose of the pharmaceutical agent in the composition is at least 10% greater than the maximum tolerated dose of the free form of pharmaceutical agent alone (e.g. formulated without the single protein).

In one embodiment, the efficacy of the pharmaceutical agent in the composition is greater than the efficacy of the pharmaceutical agent alone.

In one embodiment, the efficacy of the pharmaceutical agent in the composition is at least 10% greater than the efficacy of the pharmaceutical agent alone (e.g. formulated without the single protein).

In one embodiment, the single protein, that is tightly bound to the pharmaceutical agent has a difference in absorption, fluorescence, circular dichroism spectra, or FTIR compared to a corresponding un-tightly bound single protein.

In one embodiment, one or more molecules of the second pharmaceutical agent are tightly bound in the single protein.

In one embodiment, a plurality of molecules of the second pharmaceutical agent are encapsulated within each single protein.

In one embodiment, at least one molecule of the second pharmaceutical agent is encapsulated within each single protein.

In one embodiment, each molecule of the second pharmaceutical agent is completely encapsulated within the single protein.

In one embodiment, only part of the surface area of at least one molecule of the second pharmaceutical agent is encapsulated by the single protein.

In one embodiment, the second pharmaceutical agent has poor water solubility.

In one embodiment, the maximum tolerated dose of the second pharmaceutical agent in the composition is greater than the maximum tolerated dose of the free form of pharmaceutical agent alone (e.g. formulated without the single protein).

In one embodiment, the maximum tolerated dose of the second pharmaceutical agent in the composition is at least 10% greater than the maximum tolerated dose of the free form of pharmaceutical agent alone (e.g. formulated without the single protein).

In one embodiment, the efficacy of the second pharmaceutical agent in the composition is greater than the efficacy of the pharmaceutical agent alone (e.g. formulated without the single protein).

In one embodiment, the efficacy of the second pharmaceutical agent in the composition is at least 10% greater than the efficacy of the pharmaceutical agent alone (e.g. formulated without the single protein).

In one embodiment, the single protein that is tightly bound to the second pharmaceutical agent has a difference in absorption, fluorescence, circular dichroism spectra, or FTIR compared to a corresponding single protein that is not tightly bound to the second pharmaceutical agent.

In one embodiment, the invention provides a method for treating cancer in a human or an animal comprising administering a composition of the invention to the human or animal. In one embodiment, the therapeutic agent is doxorubicin and wherein maximum tolerated dose of the doxorubicin in the single protein composition is at least 10/o greater than the maximum tolerated dose of doxorubicin alone (e.g. formulated without the single protein).

In one embodiment, the invention provides a method comprising: Combining a first solution that comprises: water, one or more molecules of a pharmaceutical agent, and optionally one or more water soluble organic solvents, with a second solution that comprises: water, a single protein, and optionally one or more water soluble organic solvents, to provide a third solution. In one embodiment, the invention further provides sterilizing the third solution via a filtration to remove microorganisms.

The formulations of the invention may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the formulations may be combined with one or more excipients and used in the form of ingestible tablets, buccal tablets, troches, capsules, elixirs, suspensions, syrups, wafers, and the like. Such compositions and preparations should contain at least 0.1% of the formulation. The percentage of the compositions and preparations may, of course, be varied and may conveniently be between about 2 to about 60% of the weight of a given unit dosage form.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form should be pharmaceutically acceptable and substantially nontoxic in the amounts employed. In addition, the formulations may be incorporated into sustained-release preparations and devices.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride.

Sterile injectable solutions are prepared by incorporating the formulations in the required amount in the appropriate solvent with variety of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

Useful dosages of the formulations can be determined by comparing their in vitro activity, and in vivo activity in animal models. Methods for the extrapolation of effective dosages in mice, and other animals, to humans are known to the art; for example, see U.S. Pat. No. 4,938,949.

The amount of the formulation required for use in treatment will vary with the particular formulation selected, with the route of administration, with the nature of the condition being treated and with the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Formulations of the invention can also be administered in combination with other therapeutic agents. Accordingly, in one embodiment the invention also provides a composition comprising a formulation of the invention, at least one other therapeutic agent, and a pharmaceutically acceptable diluent or carrier. The invention also provides a kit comprising a formulation of the invention, at least one other therapeutic agent, packaging material, and instructions for administering the formulation and the other therapeutic agent or agents to an animal.

The unusually long half-life of HSA or IgG is maintained mainly by FcRn or the Brambell receptor (Brambell, F. W., et el., Nature, 1964, 203, 1352-1354), which is expressed in a wide variety of tissues and organs (Sockolosky, J. T., and Szoka, F. C., Adv Drug Deliv Rev, 2015, 91, 109-124). This major histocompatibility complex class I-related receptor was originally discovered to play an important role in the delivery of IgGs from the mother to the young, regulate serum IgG concentration, and maintain the long half-life of IgGs in the serum. It was later discovered that FcRn can bind both IgG and HSA at different sites and is responsible for the long half-lives of both IgGs and HAS (Chaudhury, C., J Exp Med, 2003, 197, 315-322; Anderson, C. L., et el., Trends Immunol, 2006, 27, 343-348; Chaudhury, C., et el., Biochemistry, 2006, 45, 4983-4990; and Kim, J., Bronson, et el., Am J Physiol Gastrointest Liver Physiol, 2006, 290, G352-360). As expected, FcRn mutation was found to cause familial hypercatabolic hypoproteinemia (Wani, M. A., et el., Proc Natl Acad Sci USA, 2006, 103, 5084-5089).

The mechanism of HSA rescue and recycling has been elucidated and involves:

1. FcRn binding HSA in the endosome due to high affinity at acidic pH,
2. The resulting FcRn-HSA complex (1:1 ratio) is sent back to the bloodstream,
3. The FcRn-HSA complex dissociates due to low affinity at pH 7.4, releasing HSA back in the circulation.

In cells that express low levels of FcRn, HSA would be endocytosed to lysosomes, where it is degraded to amino acids. As a result, this FcRn-mediated recycling pathway is a major factor contributing to the long half-life of both IgGs and HSA in human, and has significant pathophysiological and therapeutic implications.

From publically available protein expression databases (Uhlen, M., et el., Science, 2015, 347, 1260419; Lindskog, C., Expert Rev Proteomics, 2016, 13, 627-629; Tang, Z., Nucleic Acids Res, 2017, 45, W98-W102; Uhlen, M., Science, 2017, 357: and Papatheodorou, I., et el., Nucleic Acids Res, 2018, 46, D246-D251), differences in FcRn expression between normal and cancer tissues from different human organs was investigated. A FcRn expression comparison was made in 31 different tissues. Among them, more than half (16/31) of cancer tissues express less FcRn than their normal tissue counterparts, while about more than a quarter (12/31) of cancer tissues express more FcRn, with only 3 having similar FcRn levels. The first group (16 cancers, table 1) is the specific targets for SPE-anticancer drugs.

TABLE 1

Tumors Types Targeted for treatment (ratio of FcRn in normal/tumor tissue ≥ 1.19)

| Tumor Abbreviation | Tumor Type | Ratio of FcRn in Normal/Tumor tissue |
| --- | --- | --- |
| ACC | Adrenocortical carcinoma | 2.63 |
| BLCA | Bladder Urothelial Carcinoma | 1.81 |

TABLE 1-continued

Tumors Types Targeted for treatment (ratio of FcRn in normal/tumor tissue ≥ 1.19)

| Tumor Abbreviation | Tumor Type | Ratio of FcRn in Normal/Tumor tissue |
| --- | --- | --- |
| BRCA | Breast invasive carcinoma | 1.66 |
| CESC | Cervical squamous cell carcinoma and endocervical adenocarcinoma | 3.48 |
| CHOL | Cholangiocarcinoma | 1.75 |
| DLBC | Lymphoid Neoplasm Diffuse Large B-Lymphoma | 1.55 |
| KICH | Kidney Chromophobe | 1.92 |
| LUAD | Lung adenocarcinoma | 1.62 |
| LUSC | Lung squamous cell carcinoma | 3.14 |
| OV | Ovarian serous cystadenocarcinoma | 2.30 |
| PCPG | Pheochromocytoma and Paraganglioma | 1.33 |
| PRAD | Prostate adenocarcinoma | 1.64 |
| SARC | Sarcoma | 1.19 |
| THCA | Thyroid carcinoma | 1.39 |
| UCEC | Uterine Corpus Endometrial Carcinoma | 1.61 |
| UCS | Uterine Carcinosarcoma | 1.42 |

The invention will now be illustrated by the following non-limiting Examples.

EXAMPLES

Example 1: Targeting Effects of SPE-Anticancer Drugs

Recognizing the problems with current cancer drug formulation/delivery systems, biomacromolecules were investigated as highly efficient drug delivery systems. In particular, investigations focused on: 1) using components of all natural bio-macromolecules or proteins produced naturally or by recombinant techniques and 2) avoiding chemical modification and conjugation.

Based on this work, an SPE (Single-Protein-Encapsulation) platform for novel drug formulation was developed. For example, applying SPE to DOX encapsulation produces SPEDOX (single protein-encapsulated DOX), which contains two components, DOX and HSA. Unlike HSA-NPs that usually contains a number of HSA molecules through chemical conjugation/crosslinking or aggregation, SPEDOX provides a stable and uniform molecular system comprising a single HSA molecule that encloses a variable number of DOX molecules that can be accurately controlled.

Based on the mechanism of HSA rescue and recycling by FcRn in humans (Hoogenboezem, E. N., and Duvall, C. L., Adv Drug Deliv Rev, 2018, 130, 73-89), HSA would be taken up and endocytosed to the lysosome for hydrolysis to yield peptides and amino acids by those cells that express low levels of FcRn. Applying this concept to the SPE drug delivery platform, normal cells express normal levels of FcRn that effectively recycles SPE Drugs to maintain its long circulation in the body. If, on the other hand, a type of cancer cells expresses little or no FcRn, SPE drugs would be taken up by this type of cancer cells and endocytosed to the lysosome, where HSA is hydrolyzed and drugs are released. The resulting drug is then diffused out of the lysosome to the cytosol, where it is transported into the nucleus through the nuclear pore complexes. Therefore, a cancer type that expresses little or no FcRn (table 1) presents an ideal target for treatment with SPE-drugs.

Example 2: Preparation of Composition 1 (HSA-Encapsulated Topotecan)

Figure 1:
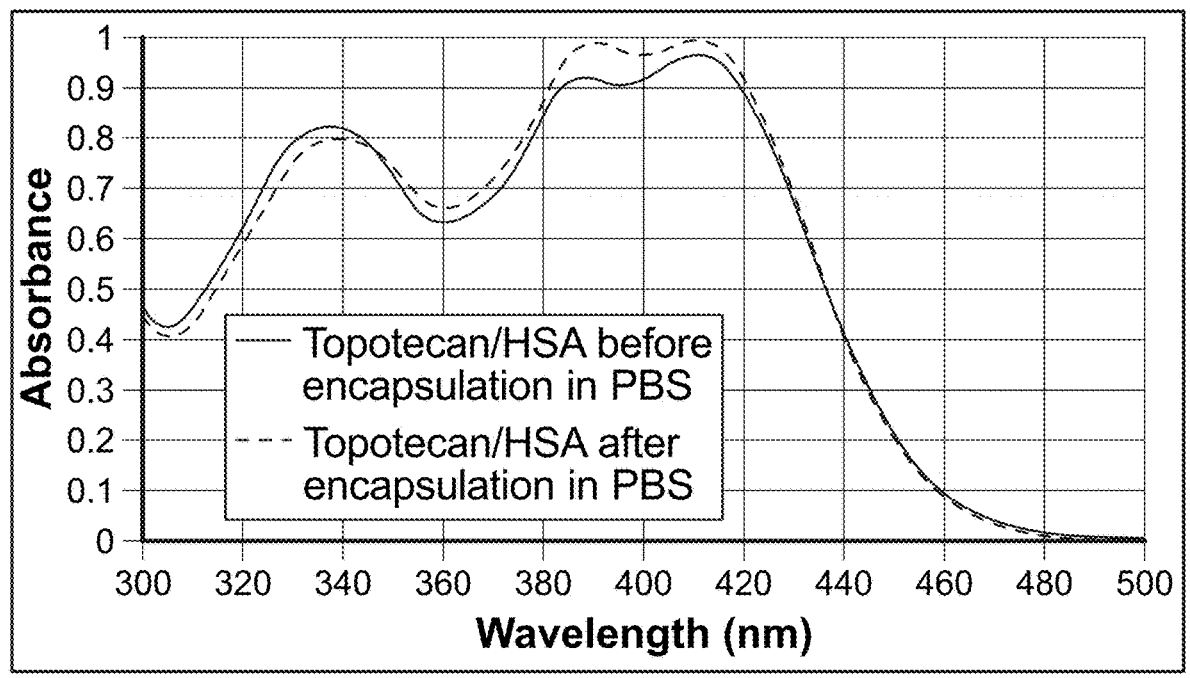
FIG. 1: Topotecan's spectral changes before and after Encapsulation in PBS (pH=7.4), see Example 2.

To 2 mL of commercial HSA solution (25% HSA) was added 2 mL of deionized water and 1 mL of 50% propylene glycol/water solution, in 50 mL round bottom flask containing a magnetic stirring bar, the mixture was stirred for 5 minutes. To a 15 mL centrifuge tube was added 25 mg of topotecan HCl salt, 1.2 mL of 50% propylene glycol/water and 3.8 mL of deionized water. After mixing well, the prepared yellowish solution was gradually added into the above HSA solution with stirring. After stirring the red mixture for 1 h at room temperature. The yellowish solution was centrifuged at 12000 RPM for 7 min, and top solution was taken and analyzed by UV spectrometer. The spectral changes of topotecan before and after encapsulation was shown FIG. 1.

Example 3: Preparation of Composition 2 (HSA-Encapsulated Epirubicin)

Figure 2:
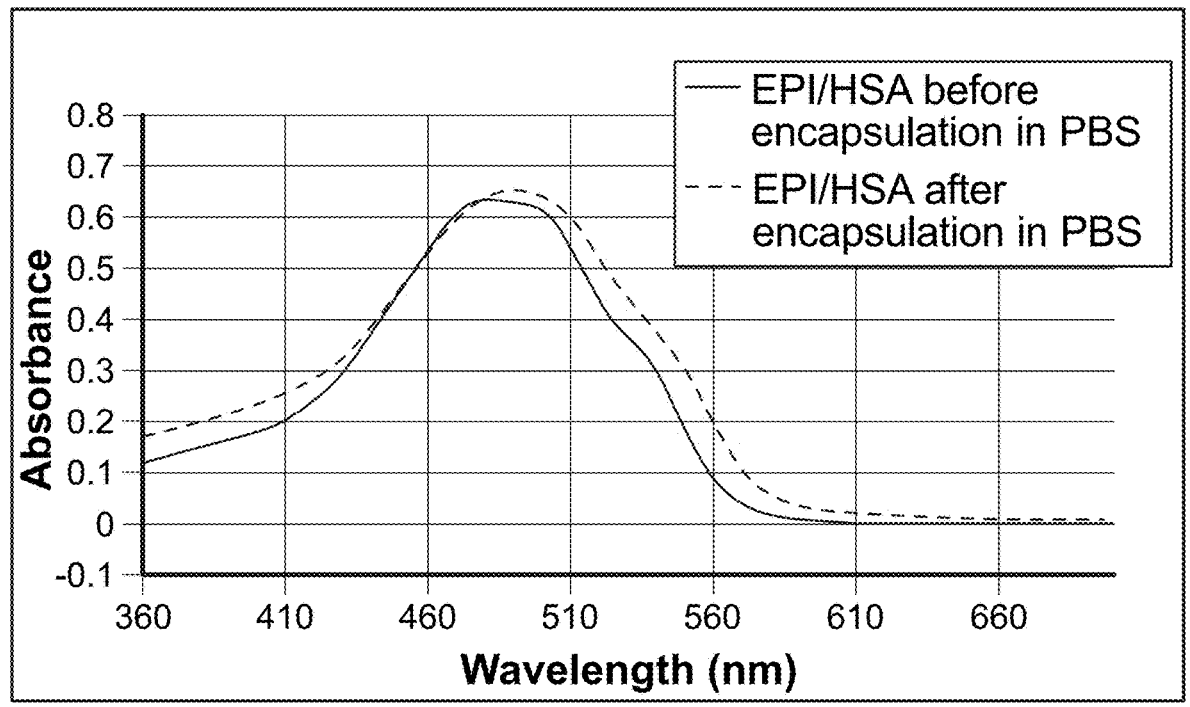
FIG. 2: Epirubicin's (EPI) spectral changes before and encapsulation in PBS (pH=7.4), see Example 3.
Figure 3:
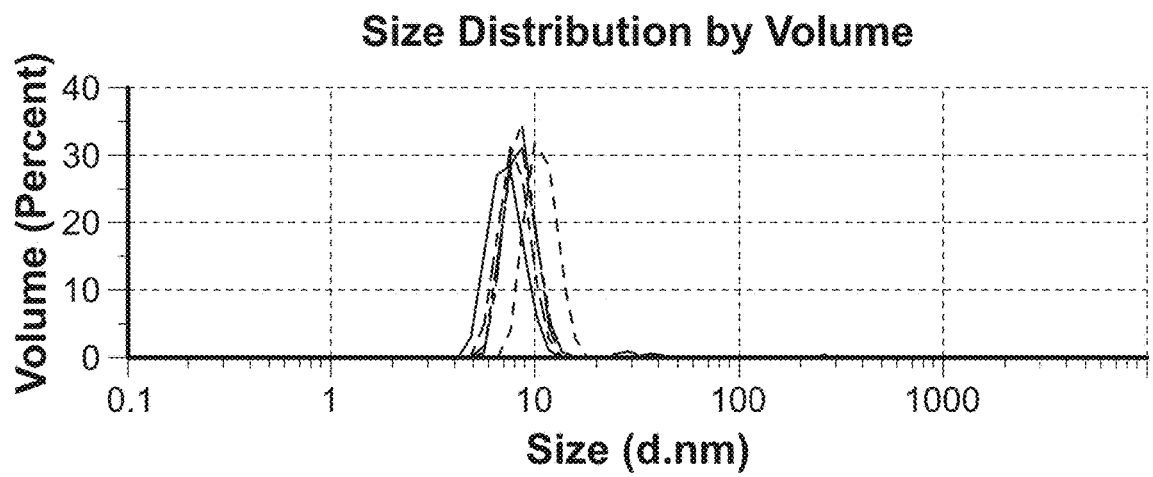
FIG. 3: HSA-encapsulated epirubicin particle size distribution by DLS, see Example 3.

To 4 mL of commercial HSA solution (25% HSA) was added 3 mL of deionized water and 1 mL of 56% ethanol/water solution, in 50 mL round bottom flask containing a magnetic stirring bar, the mixture was stirred for 5 minutes. To a 15 mL centrifuge tube was added 72 mg of epirubicin HCl salt, 2.0 mL of 56% ethanol/water and 6 mL of deionized water. After mixing well, the prepared red solution was gradually added into the above HSA solution with stirring. After stirring the red mixture for 1 hours at room temperature. The red solution was centrifuged at 12000 RPM for 10 min, and top solution was taken and analyzed by UV spectrometer and Dynamic Light Scattering instruments. The spectral changes of epirubicin before and after encapsulation was shown FIG. 2 and particle size distribution of composition 2 was shown in FIG. 3.

Example 4: Preparation of Composition 3 (HSA-Encapsulated Idarubicin)

Figure 4:
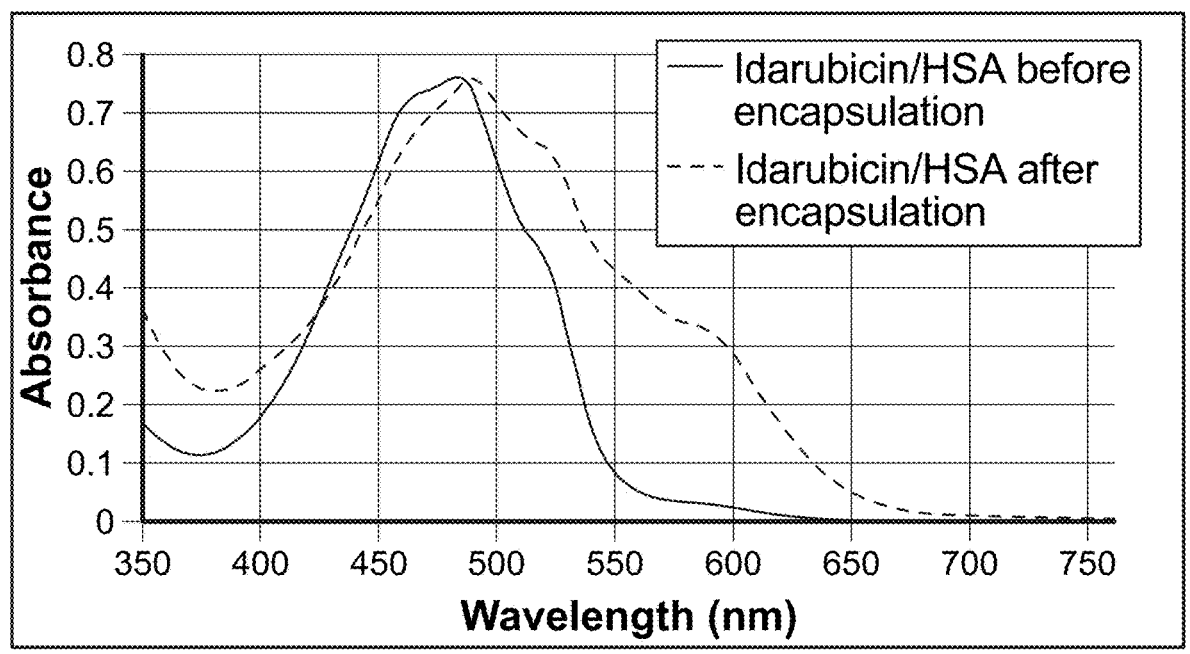
FIG. 4: Idarubicin's spectral changes before and encapsulation in PBS (pH=7.4), see Example 3.

To 2 mL of commercial HSA solution (25% HSA) was added 2 mL of deionized water and 1 mL of 50% methanol/water solution, in 50 mL round bottom flask containing a magnetic stirring bar, the mixture was stirred for 5 minutes. 1. To a 15 mL centrifuge tube was added 33 mg of idarubicin HCl salt, 3.0 mL of 50% methanol/water and 6 mL of deionized water. After mixing well, the prepared reddish solution was gradually added into the above HSA solution with stirring. After stirring the reddish mixture for 1 hours at room temperature, the mixture was concentrated to about 9 mL via a high vacuum pump, the mixture was centrifuged at 4400 RPM for 10 min. The composition 3 was further purified by Sephadex g 25 column. The purified HSA-encapsulated idarubicin was analyzed by UV spectrometer and Dynamic Light Scattering instruments. The spectral changes of idarubicin before and after encapsulation was shown FIG. 4 and particle size distribution of composition 3 was shown in FIG. 5.

Example 5: Preparation of Composition 4 (HSA-Encapsulated Vincristine)

Figure 6:
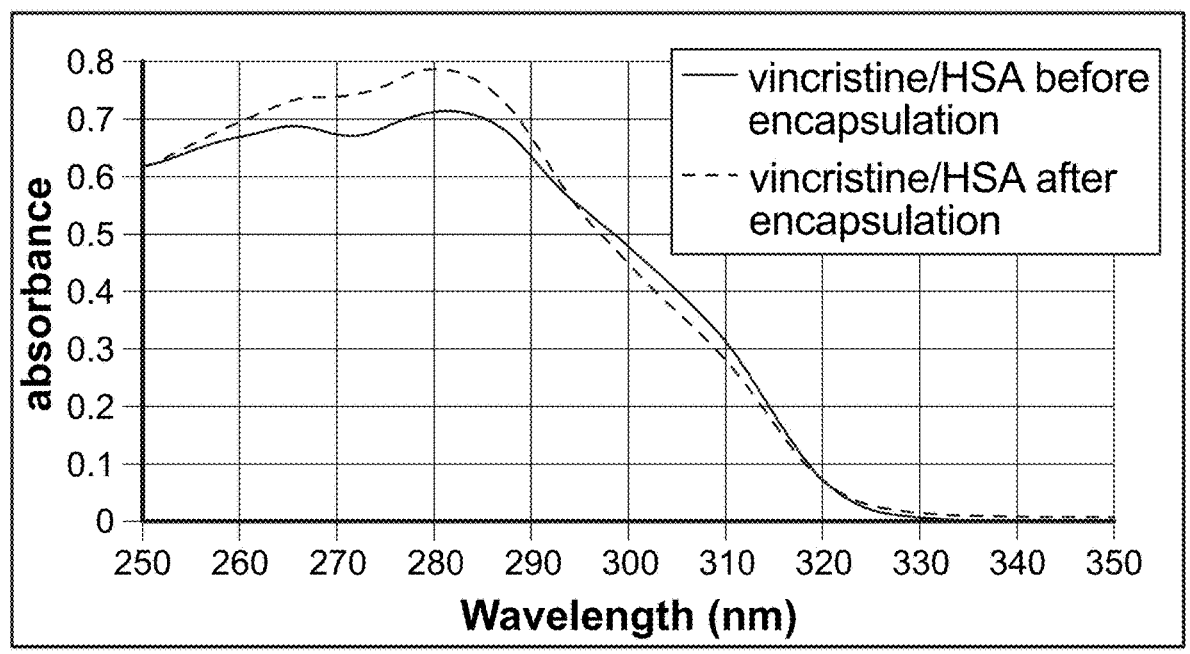
FIG. 6: Vincristine's spectral change before and after encapsulation in PBS (pH=7.4), see Example 5.

To 2 mL of commercial HSA solution (25% HSA) was added 2 mL of deionized water and 1 mL of 50% methanol/water solution, in 50 mL round bottom flask containing a magnetic stirring bar, the mixture was stirred for 5 minutes. To a 15 mL centrifuge tube was added 44 mg of vincristine. $H_2SO_4$ salt, 3.5 mL of 50% methanol/water and 6.5 mL of deionized water. After mixing well, the prepared colorless solution was gradually added into the above HSA solution with stirring. After stirring the mixture for 1 h at room temperature, the mixture was concentrated to about 8 mL via a high vacuum pump, the mixture was centrifuged at 4400 RPM for 10 minutes, the resulting solution was centrifuged at 12000 RPM for 10 minutes, and top solution was taken. The composition 4 was further purified by Sephadex g 25 column. The purified HSA-encapsulated vincristine was analyzed by UV spectrometer. The spectral changes of vincristine before and after encapsulation was shown FIG. 6.

Example 6: Preparation of Composition 5 (HSA-Encapsulated Daunorubicin)

Figure 7:
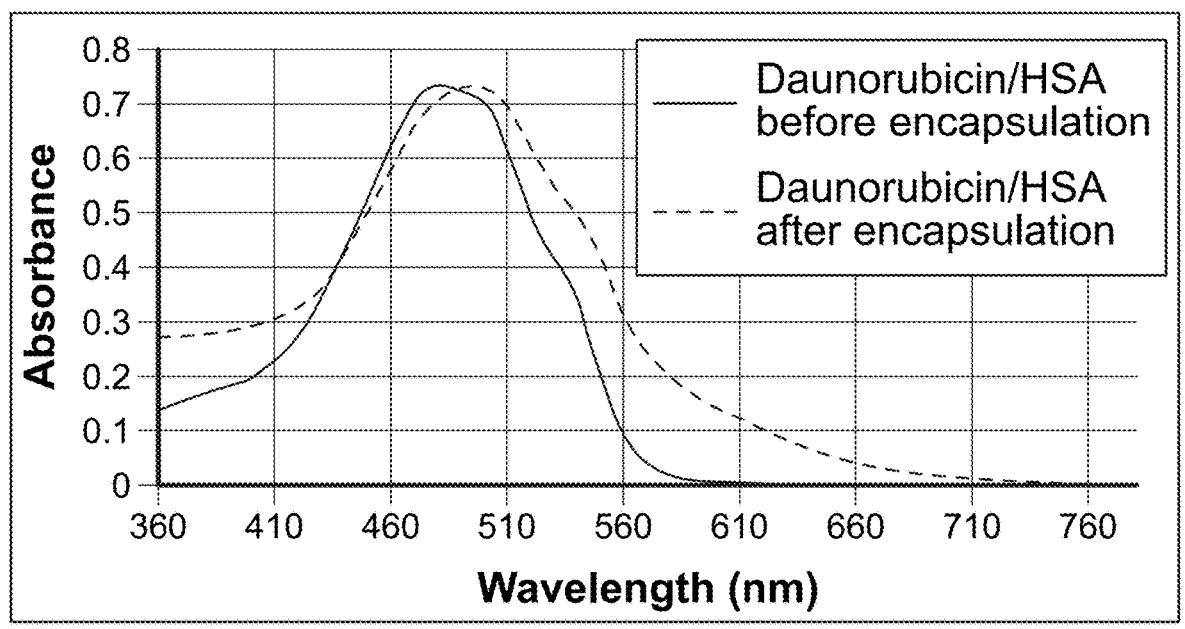
FIG. 7: Daunorubicin's UV spectral Changes before and after encapsulation in PBS (pH=7.4), see Example 6.

To 2 mL of commercial HSA solution (25% HSA) was added 2 mL of deionized water and 1 mL of 50% methanol/water solution, in 50 mL round bottom flask containing a magnetic stirring bar, the mixture was stirred for 5 minutes. To a 15 mL centrifuge tube was added 29 mg of daunorubicin HCl salt, 2.0 mL of 50% methanol/water and 6 mL of deionized water. After mixing well, the prepared red solution was gradually added into the above HSA solution with stirring. After stirring the red mixture for 1 hours at room temperature, the mixture was concentrated to about 7 mL via a high vacuum pump, the resulting solution was centrifuged at 12000 RPM for 10 min, and top solution was taken. The composition 5 was further purified by Sephadex g 25 column. The purified HSA-encapsulated daunorbicin was analyzed by UV spectrometer and Dynamic Light Scattering instruments. The spectral changes of daunorubicin before and after encapsulation was shown FIG. 7 and particle size distribution of composition 5 was shown in FIG. 8.

Example 7: Preparation of Composition 6 A (HSA-Encapsulated Mitoxantrone)

To 3 mL of commercial HSA solution (25% HSA) was added 2 mL of deionized water in 50 mL round bottom flask containing a magnetic stirring bar, the mixture was stirred for 5 minutes. To a 15 mL centrifuge tube was added 47 mg of mitoxantrone 2HCl salt, 3.0 mL of 50% methanol/water and 7 mL of deionized water. After mixing well, the prepared blue solution was gradually added into the above HSA solution with stirring. After stirring the blue mixture for 1 hours at room temperature, the mixture was concentrated to about 7 mL via a high vacuum pump, the resulting solution was centrifuged at 12000 RPM for 10 minutes, and top solution was taken. The composition 6 was further purified by Sephadex g 25 column. The purified HSA-encapsulated mitoxantrone was analyzed by UV spectrometer and Dynamic Light Scattering instruments. The spectral changes of mitoxantrone before and after encapsulation was shown FIG. 9 and particle size distribution of composition 6 was shown in FIG. 10.

Example 8: Preparation of Composition 7 (HSA-Encapsulated Doxorubicin)

To 2 mL of commercial HSA solution (25% HSA) was added 2 mL of deionized water and 1 mL of 56% ethanol/water solution, in 50 mL round bottom flask containing a magnetic stirring bar, the mixture was stirred for 5 minutes. To a 15 mL centrifuge tube was added 22 mg of doxorubicin HCl salt, 2 mL of 56% ethanol/water and 8 mL of deionized water. After mixing well, the prepared red solution was gradually added into the above HSA solution with stirring. After stirring the red mixture for 1 hours at room temperature. The red solution was centrifuged at 12000 RPM for 7 minutes, and top solution was taken and analyzed by UV spectrometer and Dynamic Light Scattering instruments. The spectral changes of doxorubicin before and after encapsulation was shown FIG. 11 and particle size distribution of composition 7 was shown in FIG. 12.

Example 9: Preparation of Composition 8 (HSA-Encapsulated Amphotericin B)

To 2 mL of commercial HSA solution (25% HSA) was added 2 mL of deionized water and 2 mL of 50% methanol/water solution, in 50 mL round bottom flask containing a magnetic stirring bar, the mixture was stirred for 5 minutes. To a 15 mL centrifuge tube was added 25 mg of amphotericin B, 2 mL of methanol and 10 mL of deionized water, followed by adding 7 drops of 1.0 M HCl solution. After mixing well, the prepared yellowish solution was gradually added into the above HSA solution. After stirring the red mixture for 1 hours at room temperature, the yellowish mixture was centrifuged at 12000 RPM for 10 min, and top solution was taken. The composition 8 was further purified by Sephadex g 25 column. The purified HSA-encapsulated amphotericin B was analyzed by UV spectrometer and Dynamic Light Scattering instruments. The spectral changes of amphotericin B before and after encapsulation was shown FIG. 13 and particle size distribution of composition 8 was shown in FIG. 14.

Example 10: Preparation of Composition 9 (HSA-Encapsulated Clofazimine)

To 2 mL of commercial HSA solution (25% HSA) was added 2 mL of deionized water and 1 mL of 56% ethanol/water solution, in 50 mL round bottom flask containing a magnetic stirring bar, the mixture was stirred for 5 minutes. To a 15 mL centrifuge tube was added 27 mg of clofazimine, 2 mL of ethanol and 2 drops of acetic acid to form a dark red solution, followed by adding 6 mL of deionized water. After mixing well, the prepared dark red solution was gradually added into the above HSA solution with stirring. After stirring the red mixture for 1 h at room temperature. The red mixture was centrifuged at 12000 RPM for 10 minutes, and top solution was taken. The solution was further centrifuged at 12000 RPM for another 10 minutes. The top solution was taken and then was analyzed by UV spectrometer and Dynamic Light Scattering instruments. The spectral changes of clofazimine before and after encapsulation was shown FIG. 15.

Example 11: Preparation of Composition 10 (HSA-Encapsulated Methotrexate)

Figure 16:
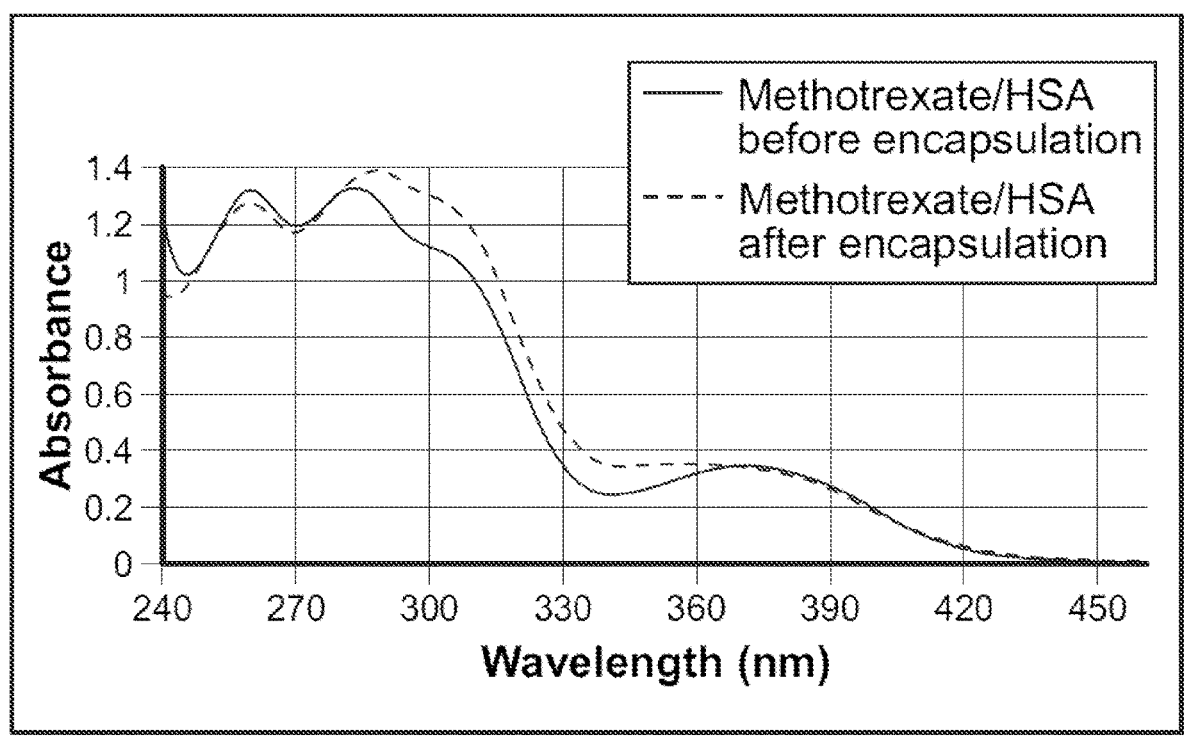
FIG. 16: Methotrexate's spectral changes before and after encapsulation in PBS, (pH=7.4), see Example 11.

To 2 mL of commercial HSA solution (25% HSA) was added 2 mL of deionized water and 1 mL of 50% methanol/water solution, in 50 mL round bottom flask containing a magnetic stirring bar, the mixture was stirred for 5 minutes. To a 15 mL centrifuge tube was added 31 mg of methotrexate, 2.0 mL of 50% methanol/water and 7 mL of deionized water. After mixing well, the prepared yellowish solution was gradually added into the above HSA solution with stirring. After stirring the red mixture for 1 h at room temperature, HSA-encapsulated methotrexate was analyzed by UV spectrometer and Dynamic Light Scattering instruments. The spectral changes of methotrexate before and after encapsulation was shown FIG. 16 and particle size distribution of composition 10 was shown in FIG. 17.

Example 12: Preparation of Composition 11 (HSA-Encapsulated Rifampicin)

Figure 18:
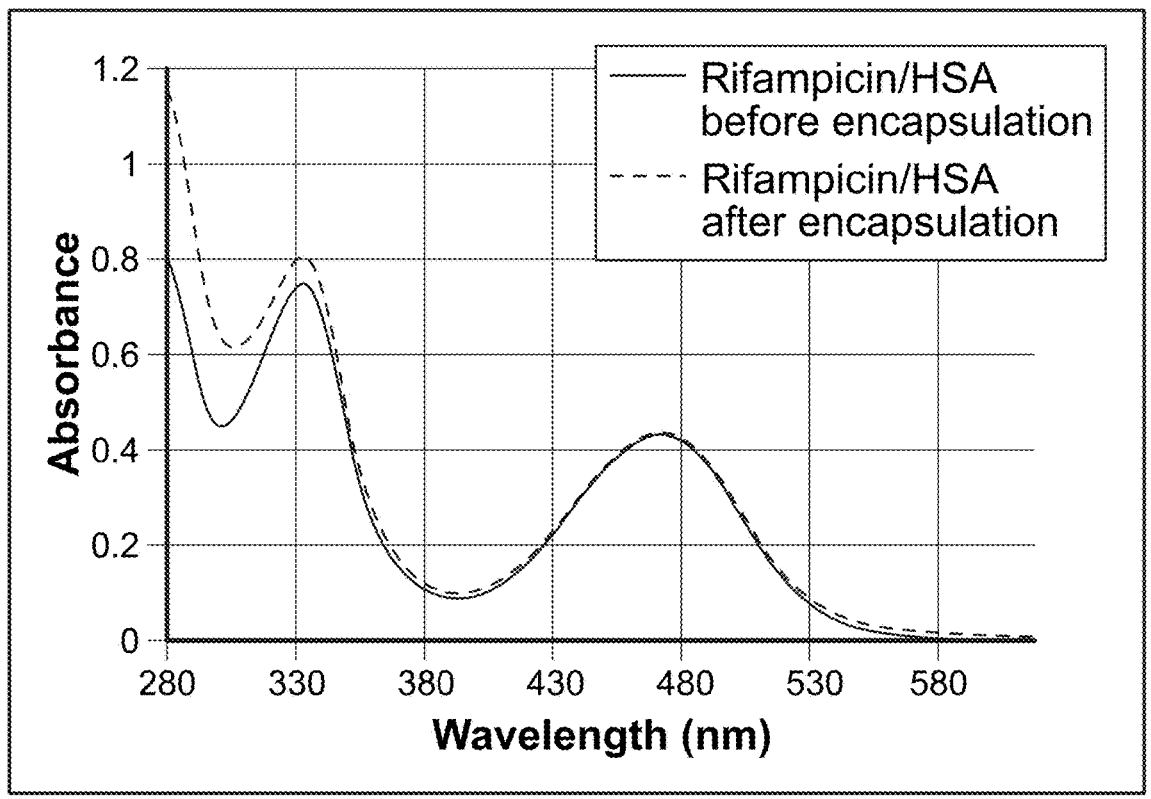
FIG. 18: Rifampicin's spectral changes before and after encapsulation in PBS (pH=7.4), see Example 12.

To 2 mL of commercial HSA solution (25% HSA) was added 9 mL of deionized water and 1 mL of 50% methanol/water solution, in 50 mL round bottom flask containing a magnetic stirring bar, the mixture was stirred for 5 minutes. To a 15 mL centrifuge tube was added 44 mg of rifampicin, 2.0 mL of methanol and 1 mL of water. After mixing well, the prepared red solution was gradually added into the above HSA solution with stirring. After stirring the red mixture for 2 hours at room temperature, the red mixture was centrifuged at 12000 RPM for 10 min, and top solution was taken, which was further purified by Sephadex g 25 column. The purified HSA-encapsulated rifampicin was analyzed by UV spectrometer. The spectral changes of rifampicin before and after encapsulation was shown FIG. 18.

Example 13: Preparation of Composition 12 (HSA-Encapsulated Vinblastine)

Figure 19:
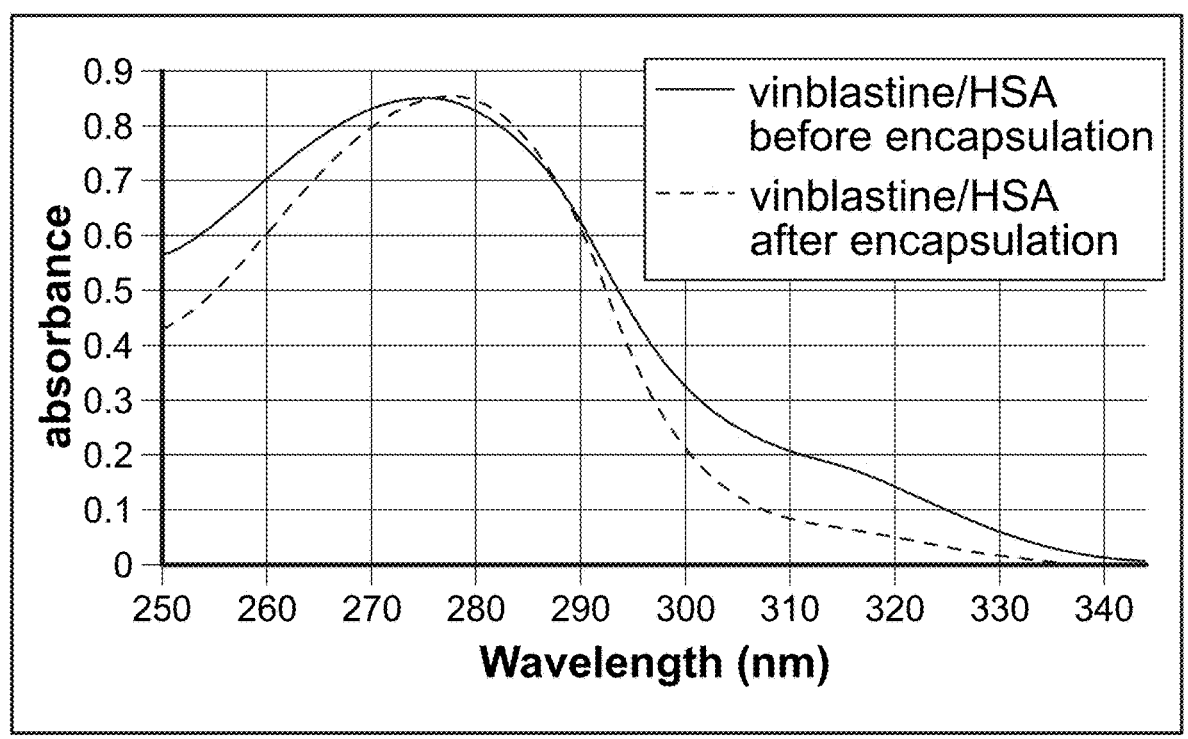
FIG. 19, Vinblastine's spectral changes before and after encapsulation in PBS (pH=7.4), see Example 13.

To 2 mL of commercial HSA solution (25% HSA) was added 3 mL of deionized water and 6 mL of 50% methanol/water solution, in 50 mL round bottom flask containing a magnetic stirring bar, the mixture was stirred for 5 minutes. To a 15 mL centrifuge tube was added 46 mg of vinblastine, 9.0 mL of 50% methanol/water. After mixing well, the prepared solution was gradually added into the above HSA solution with stirring. After stirring the mixture for 2 hours at room temperature, the mixture was concentrated to about 2 mL via a high vacuum pump. After adding another 8 mL of di-water, the mixture was centrifuged at 4400 RPM for 10 min and the top solution was taken and centrifuged at 12000 RPM for 7 min. The HSA-encapsulated vinblastine was analyzed by UV spectrometer. The spectral changes of vinblastine before and after encapsulation was shown FIG. 19.

Example 14: Preparation of Composition 13 (HSA-Encapsulated Vinorelbine)

Figure 20:
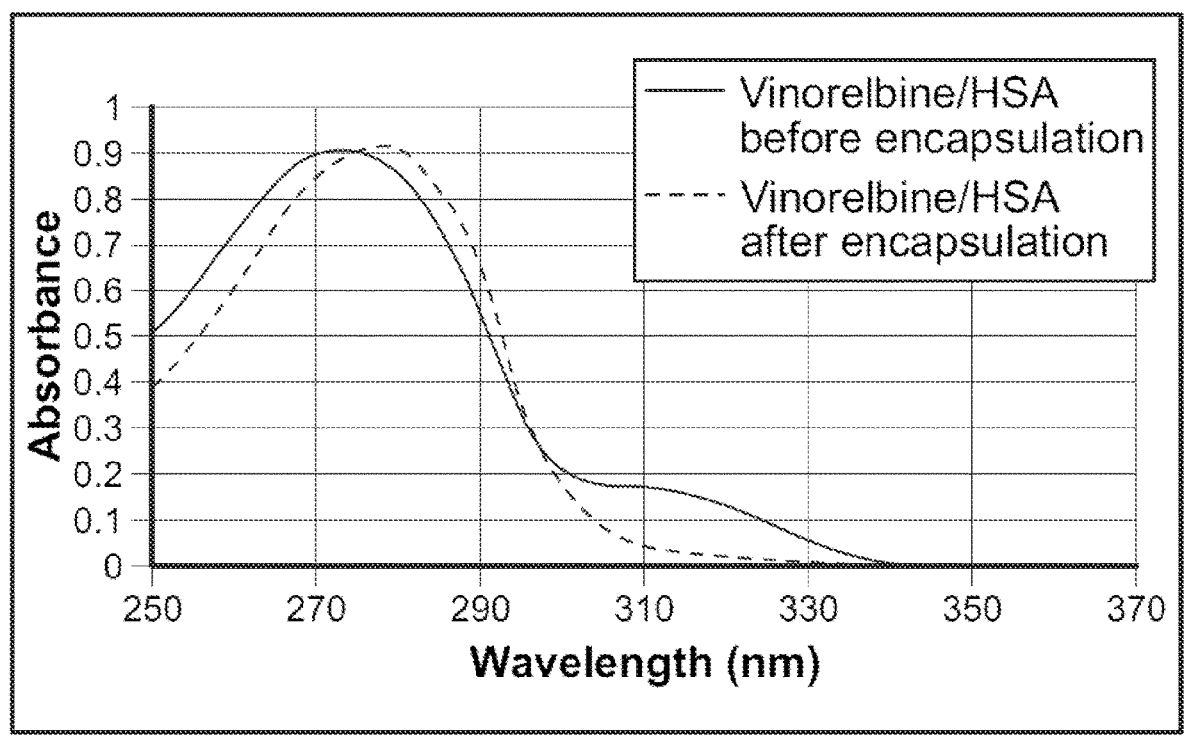
FIG. 20, Vinorelbine's spectral changes before and after encapsulation in PBS (pH=7.4), see Example 14.

To 2 mL of commercial HSA solution (25% HSA) was added 2 mL of deionized water, 1 mL of methanol and 5 mL of 50% methanol/water solution, in 50 mL round bottom flask containing a magnetic stirring bar, the mixture was stirred for 5 minutes. To a 15 mL centrifuge tube was added 44 mg of vinorelbine, 9.0 mL of 50% methanol/water. After mixing well, the prepared solution was gradually added into the above HSA solution with stirring. After stirring the mixture for 2 h at room temperature, the mixture was concentrated to about 2 mL via a high vacuum pump. After adding another 8 mL of di-water, the mixture was centrifuged at 4400 RPM for 10 min and the top solution was taken and centrifuged at 12000 RPM for 8 min. The HSA-encapsulated vinorelbine was analyzed by UV spectrometer. The spectral changes of vinblastine before and after encapsulation was shown FIG. 20.

Example 15: Preparation of Composition 14 (HSA-Encapsulated Paclitaxel)

To 2 mL of commercial HSA solution (25% HSA) was added 6 mL of deionized water in 50 mL round bottom flask containing a magnetic stirring bar, followed by 3 mL of methanol and 5 mL of 50% methanol/water solution, the mixture was stirred for 5 min. To a 15 mL centrifuge tube was added 40 mg of paclitaxel, 3.0 mL of methanol and 7 mL of 50% methanol/water. After mixing well, the prepared solution was gradually added into the above HSA solution with stirring. After stirring the mixture for 1 h at room temperature, the mixture was concentrated to about 2 mL via a high vacuum pump. After adding another 8 mL of di-water, the mixture was centrifuged at 12000 RPM for 10 min, and top solution was taken, which was further purified by Sephadex g 25 column.

Example 16: Dialysis Study on the Free Form of Doxorubicin, HSA/DOX Mixture and Composition 7

Figure 22:
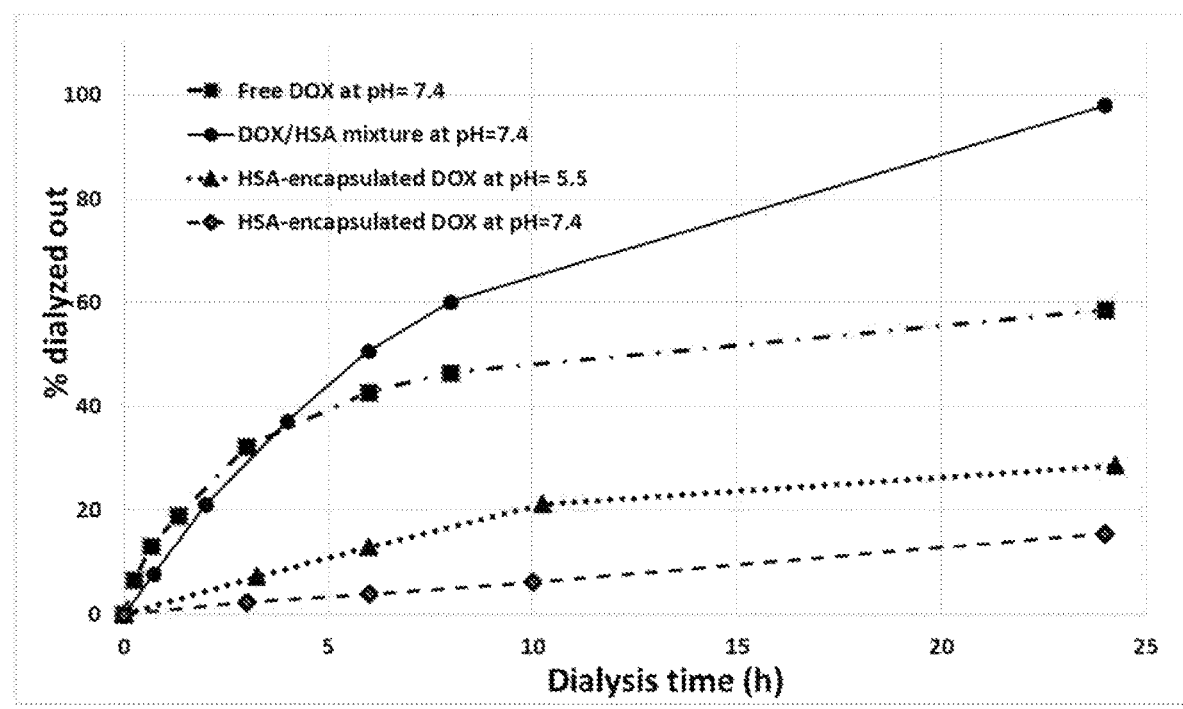
FIG. 22: Time profile of dialysis of free form of doxorubicin, HSA/DOX mixture and HSA-encapsulated DOX at different pH values, see Example 16.

To a 3×3 cm flat dialysis tube (molecular weight cut: 25 kD) was added a red solution of 3 mg of free form of doxorubicin, 3 mg of doxorubicin equivalent of HSA/DOX mixture or 3 mg of doxorubicin equivalent of composition 7 in 2 mL of di-water. The dialysis tube was sealed and put into a glass beaker containing 100 mL of either PBS buffer (pH=7.4) or acetate buffer (pH=5.5) with a magnetic stirring bar. With constant stirring, aliquots (500 uL) at different time points were taken from the glass beaker and analyzed by UV spectrometer. The percent of the dialyzed out from the dialysis tubes at different pH values was calculated and shown in FIG. 22. It is very clear that HSA/DOX mixture was dialyzed out almost 100% at pH=7.4 within 24 h; for free form of doxorubicin at pH=7.4, it was dialyzed out very fast in the earlier time and but it precipitated in the dialysis bag due to the poor solubility at pH=7.4. It is most interesting to notice that HSA-encapsulated DOX is almost 3.5 times faster at pH=5.5 than at pH=7.4 for being dialyzed out from the dialysis tube.

Example 17: Efficacy Study

Figure 23:
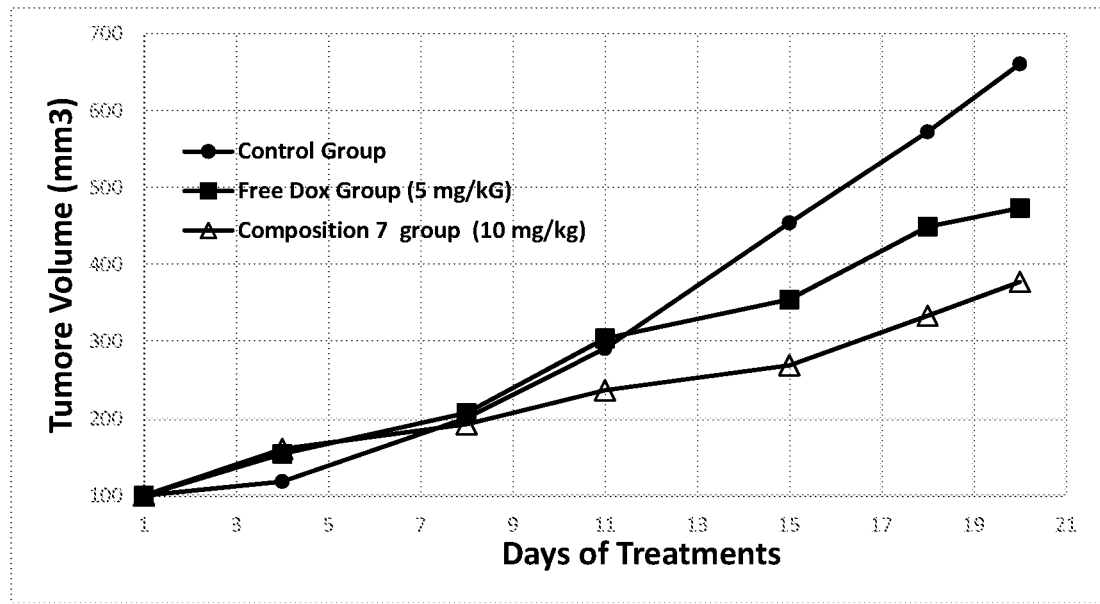
FIG. 23: Mean tumor volume changes vs Days of treatments by control, free Dox and Composition 7, see Example 17.
Figure 24:
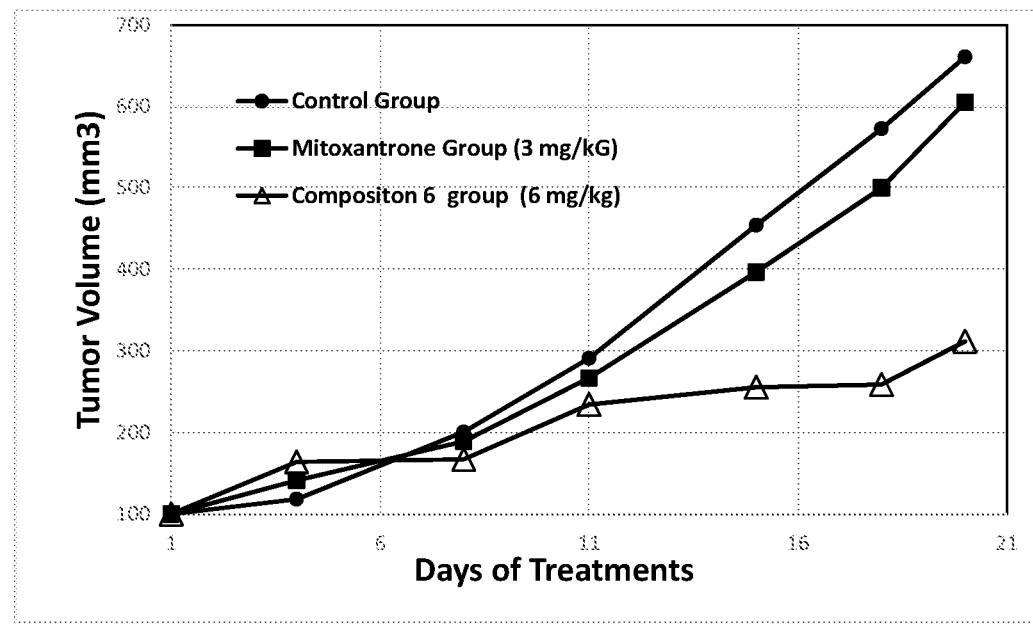
FIG. 24: Mean tumor volume changes vs Days of treatments by control, free mitoxantrone and Composition 6, see Example 17.
Figure 25:
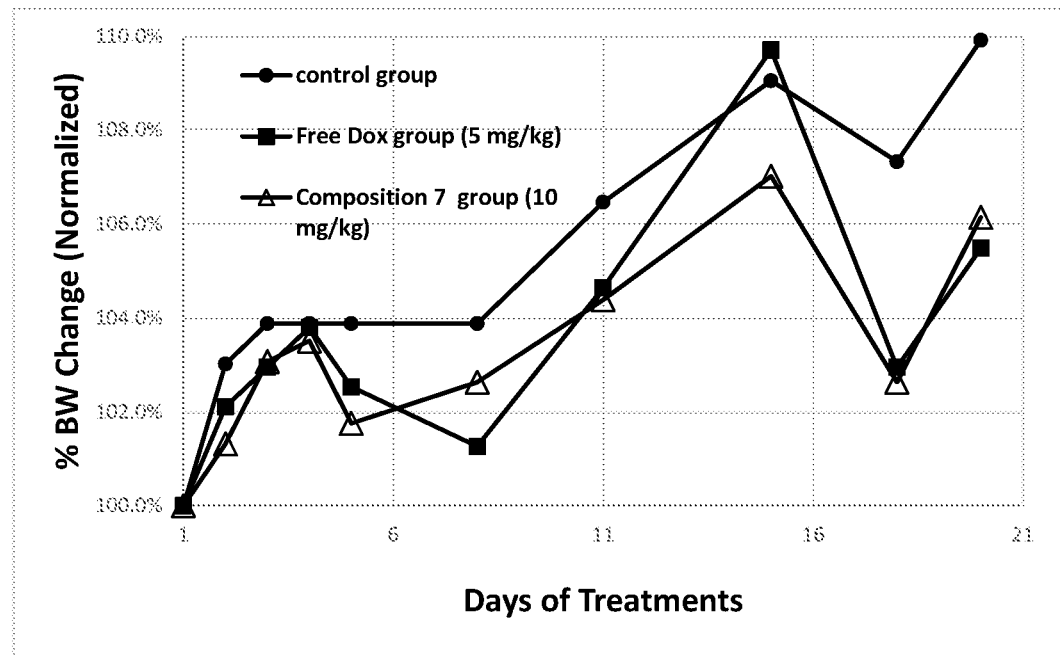
FIG. 25: % Body weight Changes (Normalized) vs Days of treatments by control, free Dox and Composition 7, see Example 17.
Figure 26:
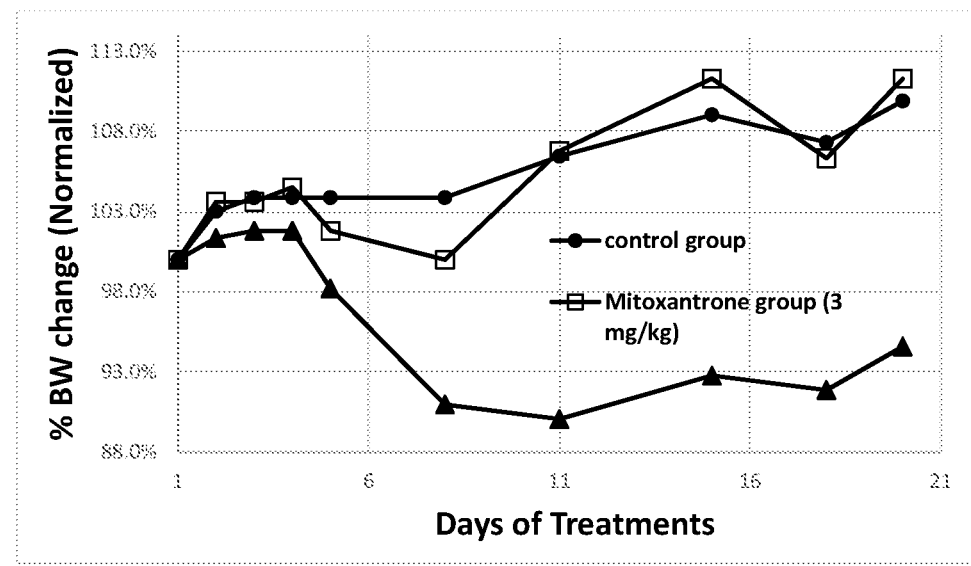
FIG. 26: % Body weight Changes (Normalized) vs Days of treatments by control, mitoxantrone and Composition 6, see Example 17.

An efficacy study against breast cancer tumor was carried out on the materials from Example 8 (Composition 7) and Example 7 (Composition 6). It is documented that he maximum tolerated dose (MTD) of free DOX in a mouse model is 5 mg/kg and the MTD of free mitroxantrone is 3 mg/kg. The results of a xenograft model efficacy study using breast cancer cell line, MDA-MB231, in female athymic nude mice, free DOX as 5 kg/mL, and material from Example 7 as 10 mg/kg (DOX equivalent, 2× of MTD of the free DOX), material from Example 6, as 6 mg/kg (mitoxantrone equivalent, 2× of MTD of the free mitoxantrone) are shown in 1, FIG. 23 and FIG. 24. For doxorubicin, HSA-tightly bound Dox, is significantly better than free DOX in inhibiting tumor growth (p<0.05); with % TGI at 54% for the material from sample 7 vs 34 for free DOX. For mitoxantrone, HSA-tightly bound mitoxantrone, is significantly much better than free mitoxantrone in inhibiting tumor growth (p<0.01); with % TGI at 58% for the material from sample 6 vs 27 for free mitoxantrone. Furthermore, by comparing the body weight changes (normalized), shown in FIG. 25 and FIG. 26, Composition 7, though 2× of DOX equivalents, did not show any toxicity (FIG. 25), however; Composition 6 from Example 7, though 2× of mitoxantrone equivalents, show some acceptable toxicity (only average 10% body weight loss, see FIG. 26). Results are shown in Table 2 for representative compositions.

TABLE 2

Tumor Growth Inhibition in MDA-MB-231 Study using Composition 6 and Composition 7

| Group | n | Treatment Regimen Agent | mg/kg | Route | Schedule | MTV (n) Day 20 | % TGI | Statistical Significance vs G1 | vs G3 | vs G5 | Regressions PR | CR | Mean BW Nadir | Deaths TR | NTR |
|---|---|---|---|---|---|---|---|---|---|---|---|---|---|---|---|
| 1 | 8 | vehicle | — | iv | qwk × 3 | 683 (8) | — | — | — | — | 0 | 0 | — | 0 | 0 |
| 2 | 8 | Doxorubicin | 5 | iv | qwk × 3 | 453 (8) | 34 | ns | ns | — | 0 | 0 | — | 0 | 0 |
| 3 | 8 | Composition 7 | 10 | iv | qwk × 3 | 311 (8) | 54 | * | — | — | 0 | 0 | — | 0 | 0 |
| 4 | 8 | Mitoxantrone | 3 | iv | qwk × 3 | 498 (8) | 27 | ns | — | * | 0 | 0 | −0.2% Day 8 | 0 | 0 |
| 5 | 7 | Composition 6 | 6 | iv | qwk × 3 | 288 (7) | 58 | ** | — | — | 0 | 0 | −8.7% Day 8 | 0 | 1 |

Figure 27:
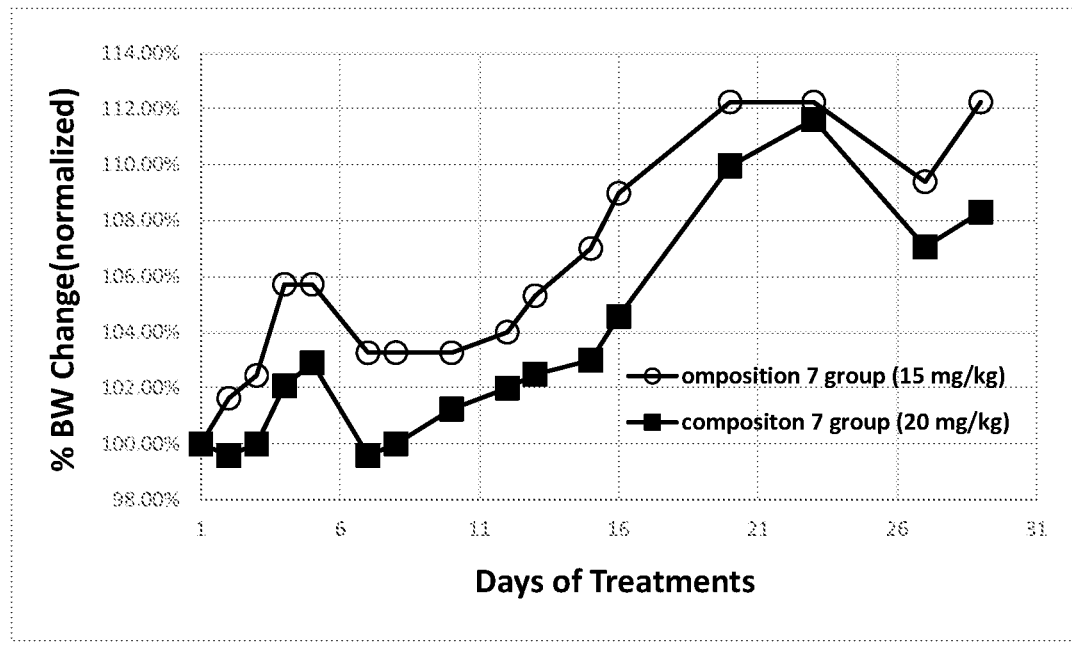
FIG. 27: % Body weight Changes (Normalized) vs Days of treatments by 3× (15 mg/kg) and 4× (20 mg/kg) of Dox equivalents in Composition 7, see Example 18.

The abovetTable displays the final treatment regimen at the completion of the study.
vehicle = Sterile Water
Study Endpoint = 2000 mm$^3$; Study Duration = 20 Days
n = number of animals in a group not dead from accidental or unknown causes, or euthanized for sampling
% TGI = [1 − (MTV$_{drug\ treated}$/MTV$_{control}$)] × 100 = percent tumor growth inhibition, compared to Group 1
Stastical Significance (Mann-Whitney U test): ne = not evaluable, ns = not significant,
* = P ≤ 0.05,
** = P ≤ 0.01,
*** = P ≤ 0.001, compared to Group 1
MTV (n) = median tumor volume (mm$^3$) for the number of animals on the Day of TGI analysis (includes animals with tumor volume at endpoint)
PR = partial regression;
CR = complete regression
Mean BW Nadir = lowest group mean body weight, as % change from Day 1;
— indicates no decrease in mean body weight was observed
TR = treatment-related death;
NTR = non-treatment related death Example 18: Toxicity Study In order to investigate toxicity of Composition 7, a MTD study using health female athymic nude mice (4 mice per group) with the same route and schedule like the efficacy study (Example 13), was conducted and completed. The resulting data is shown in FIG. 27. These data demonstrate that 3 times and 4 times of DOX equivalents in the material from Composition 7 did not show toxicity.

Example 19: Second MTD Study

Figure 28:
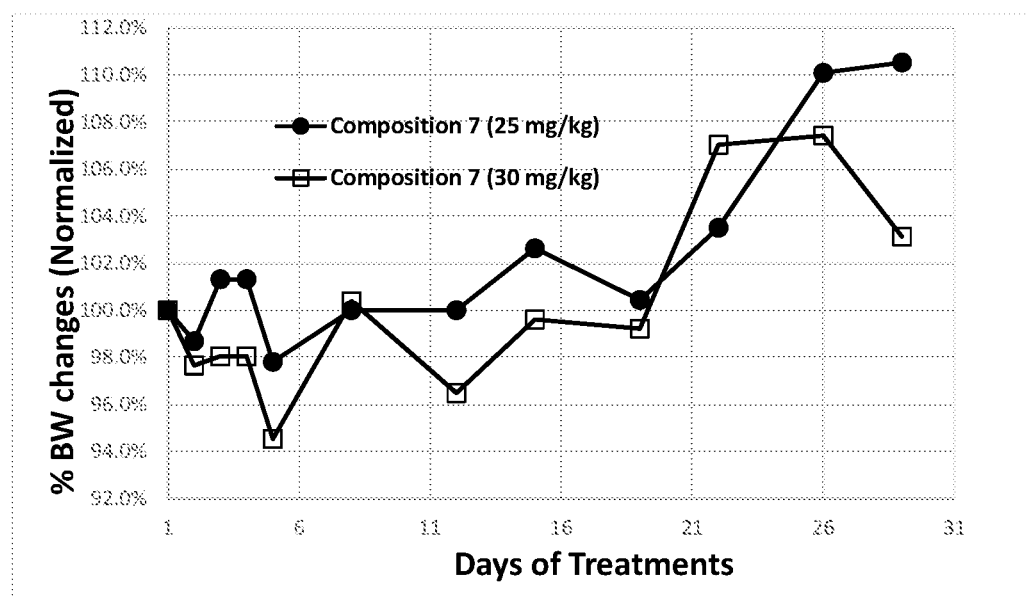
FIG. 28: % Body weight Changes (Normalized) vs Days of treatments by 5× (25 mg/kg) and 6× (30 mg/kg) of Dox equivalents in Composition 7, see Example 19.

A second MTD study using the same protocols, with varied doses was also completed. The resulting data is presented in FIG. 28. These data demonstrate that 5 times and 6 times of DOX equivalents in Composition 7 are still very safe.

Example 20: Preparation of Composition 15 (IGG-Encapsulated Doxorubicin)

Figure 21:
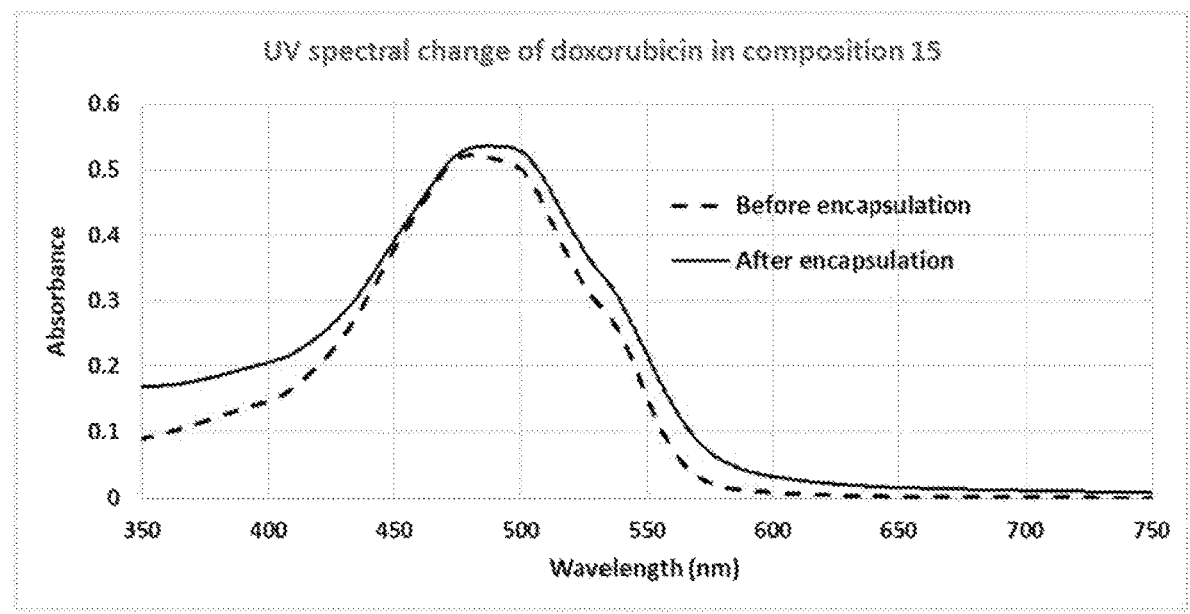
FIG. 21: UV spectral changes of doxorubicin in composition 15, see Example 20.

To 35 mg of doxorubicin hydrochloride was added 10 mL of Deionized water, after shaking well, the red solution was formed. Into this solution was added 500 mg of IgG antibody powder, the mixture was stirred for 1 hour and the red solution was prepared. And then 4.0 mL of 50% ethanol/$H_2O$ was added. The mixture was stirred for 1 h and mixture was centrifuged at 4400 RPM for 12 minutes, the top solution was taken and the pH was adjusted 7.3 by adding 0.5 M HCl solution. The IgG-encapsulated doxorubicin (composition 15) was analyzed by UV spectrometer. The spectral changes of doxorubicin before and after encapsulation was shown in FIG. 21.

Example 21: Preparation of Composition 16 (IGG-Encapsulated Epirubicin)

Figure 33:
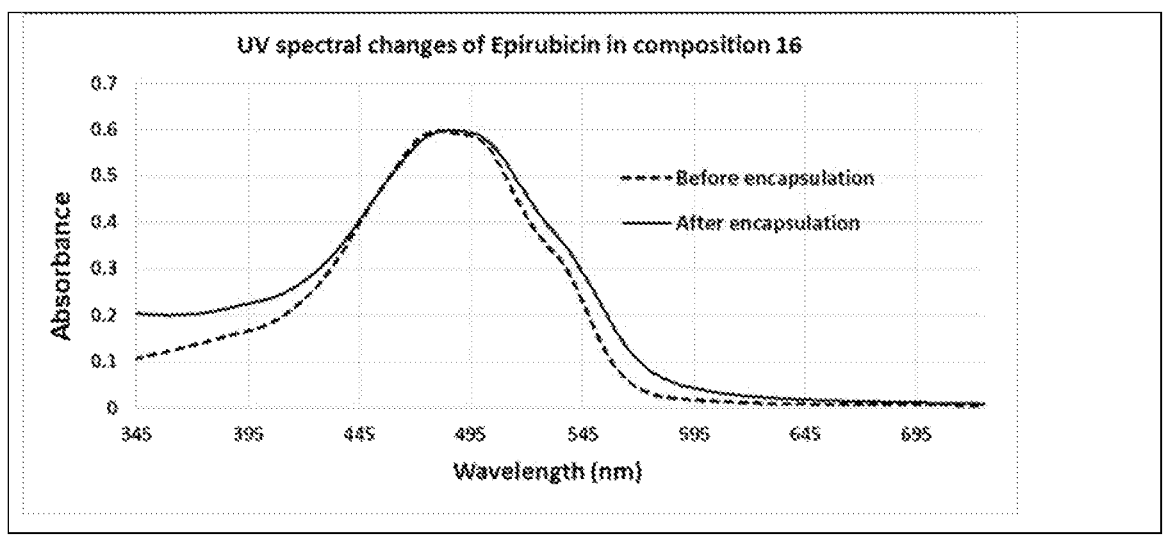
FIG. 33: UV spectral changes of epirubicin in composition 16, see Example 21.

To 28 mg of epirubicin hydrochloride was added 12 mL of Deionized water, after shaking well, the red solution was formed. Into this solution was added 500 mg of IgG antibody powder, the mixture was stirred for 1 hour and the red solution was prepared. And then 5.0 mL of 50% ethanol/$H_2O$ was added. The mixture was stirred for 1 hour and mixture was centrifuged at 4400 RPM for 12 minutes, the top solution was taken. The IgG-encapsulated epirubicin (composition 16) was analyzed by UV spectrometer. The spectral changes of doxorubicin before and after encapsulation was shown FIG. 33.

Example 22: Preparation of Composition 17 (HSA-Encapsulated Docetaxel)

To 6.5 mL of commercial HSA solution (25% HSA) was added 12.5 mL of deionized water and 8.5 mL of 50% tert-butanol/water solution, in 50 mL round bottom flask containing a magnetic stirring bar, the mixture was stirred for 5 minutes. To a 15 mL centrifuge tube was added 71 mg of docetaxel, 3.0 mL of ethanol. The resulting docetaxel solution was added into the above HSA. After stirring the mixture for 2 hours at room temperature, the mixture was centrifuged at 4400 RPM for 10 minutes and the top solution was taken. After lyophilizing, HSA-encapsulated docetaxel (composition 17) powder was obtained.

Example 23: Preparation of Composition 18 (HSA-Encapsulated Doxorubicin and Docetaxel)

Figure 34:
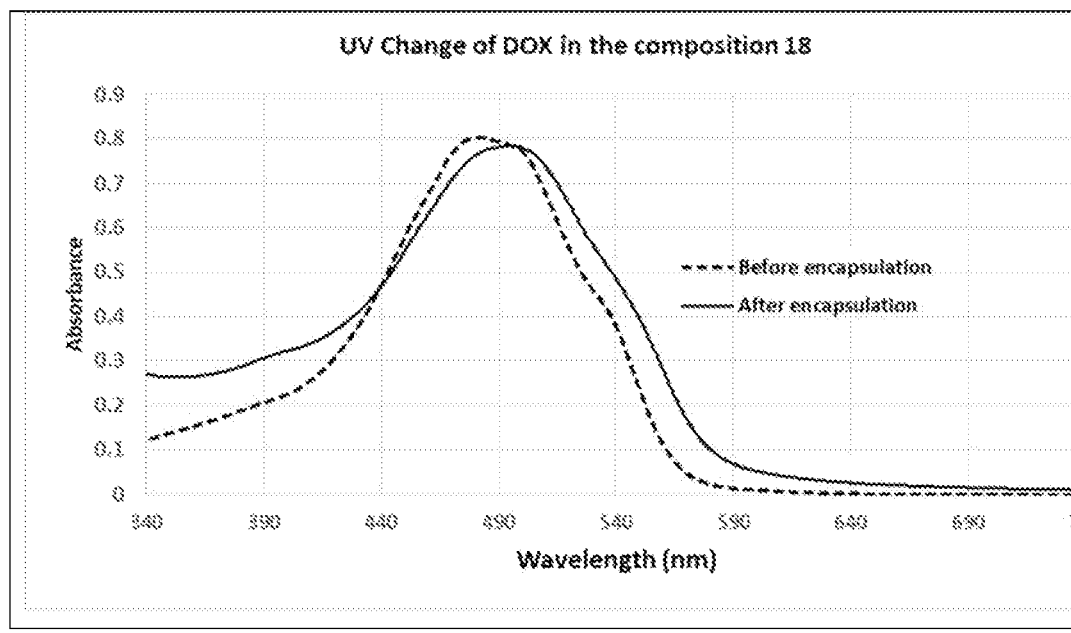
FIG. 34: UV spectral changes of doxorubicin in composition 18, see Example 23.

To 66 mg of doxorubicin hydrochloride was added 14 mL of Deionized water, after shaking well, the red solution was formed. Into this solution was added 1.6 g of HSA powder, the mixture was stirred for 20 minutes and then 6.0 mL of 50% ethanol/$H_2O$ was added. The mixtures was stirred for 30 minutes. In another 15 mL of centrifuge tube was added 46 mg of docetaxel and 3 ml of ethanol. The resulting docetaxel solution was added into the above red solution. The mixture was stirred for 2 hours and mixture was centrifuged at 4400 RPM for 10 minutes, the top solution was taken The HSA-encapsulated doxorubicin and docetaxel (composition 18) was analyzed by UV spectrometer. The spectral changes of doxorubicin before and after encapsulation was shown FIG. 34. After lyophilizing, the composition 18 powder form was obtained.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A composition, comprising a single protein selected from the group consisting of an albumin, a globulin, and a fibrinogen, having tightly bound therein, a plurality of molecules of doxorubicin.

2. The composition of claim 1, wherein the single protein is human albumin or IGG.

3. A composition, comprising the single protein human albumin having tightly bound therein a plurality of molecules of doxorubicin.

* * * * *